US012351685B2

(12) United States Patent
Eguchi et al.

(10) Patent No.: US 12,351,685 B2
(45) Date of Patent: *Jul. 8, 2025

(54) POLYAMIDE ACID, POLYIMIDE, OPTICAL FILM, DISPLAY DEVICE AND PRODUCTION METHODS THEREOF

(71) Applicant: Central Glass Company, Limited, Ube (JP)

(72) Inventors: Hiroshi Eguchi, Kawagoe (JP); Ayumi Yamaguchi, Kawagoe (JP); Yukari Hara, Kawagoe (JP); Kei Matsunaga, Kawagoe (JP); Hiroto Hori, Kawagoe (JP); Yosuke Murakami, Kawagoe (JP); Kensuke Hirotaki, Kawagoe (JP); Kenji Hosoi, Kawagoe (JP)

(73) Assignee: Central Glass Company, Limited, Ube (JP)

( * ) Notice: Subject to any disclaimer, the term of this patent is extended or adjusted under 35 U.S.C. 154(b) by 809 days.

This patent is subject to a terminal disclaimer.

(21) Appl. No.: 17/428,860

(22) PCT Filed: Feb. 3, 2020

(86) PCT No.: PCT/JP2020/003969
§ 371 (c)(1),
(2) Date: Aug. 5, 2021

(87) PCT Pub. No.: WO2020/162411
PCT Pub. Date: Aug. 13, 2020

(65) Prior Publication Data
US 2022/0119595 A1    Apr. 21, 2022

(30) Foreign Application Priority Data
Feb. 6, 2019    (JP) .................. 2019-019823

(51) Int. Cl.
| C08G 73/10 | (2006.01) |
| C07B 61/00 | (2006.01) |
| C07C 17/266 | (2006.01) |
| C07C 17/32 | (2006.01) |
| C07C 22/08 | (2006.01) |
| C07C 37/20 | (2006.01) |
| C07C 37/62 | (2006.01) |
| C07C 39/16 | (2006.01) |
| C07C 41/30 | (2006.01) |
| C07C 43/225 | (2006.01) |
| C07C 45/63 | (2006.01) |
| C07C 201/12 | (2006.01) |
| C07C 205/22 | (2006.01) |
| C07C 209/78 | (2006.01) |
| C07C 211/56 | (2006.01) |
| C07C 213/08 | (2006.01) |
| C07C 215/80 | (2006.01) |
| C08G 73/12 | (2006.01) |
| C08J 5/18 | (2006.01) |

(52) U.S. Cl.
CPC .......... *C08G 73/1039* (2013.01); *C07C 17/32* (2013.01); *C07C 22/08* (2013.01); *C07C 37/62* (2013.01); *C07C 39/16* (2013.01); *C07C 41/30* (2013.01); *C07C 43/225* (2013.01); *C07C 201/12* (2013.01); *C07C 205/22* (2013.01); *C07C 209/78* (2013.01); *C07C 211/56* (2013.01); *C07C 213/08* (2013.01); *C07C 215/80* (2013.01); *C08G 73/1028* (2013.01); *C08G 73/1078* (2013.01); *C08G 73/123* (2013.01)

(58) Field of Classification Search
None
See application file for complete search history.

(56) References Cited

U.S. PATENT DOCUMENTS

| 3,179,614 | A | * | 4/1965 | Edwards | ............ C08G 73/1007 |
| | | | | | 524/718 |
| 3,388,097 | A | | 6/1968 | Cramer | |
| 3,770,573 | A | * | 11/1973 | Dunphy | .................... C08J 7/043 |
| | | | | | 428/339 |
| 4,365,098 | A | | 12/1982 | Mark et al. | |
| 4,467,121 | A | | 8/1984 | Mark et al. | |
| 4,803,147 | A | | 2/1989 | Mueller et al. | |
| 7,825,280 | B2 | | 11/2010 | Saegusa et al. | |
| 7,932,348 | B2 | | 4/2011 | Saegusa et al. | |

(Continued)

FOREIGN PATENT DOCUMENTS

| CN | 106832278 A | 6/2017 |
| GB | 1036870 | 7/1966 |
| JP | 57-502055 A | 11/1982 |
| JP | 2-870 A | 1/1990 |
| JP | 2002-356615 A | 12/2002 |
| JP | 2007-119504 A | 5/2007 |
| JP | 2016-76480 A | 5/2016 |
| JP | 2016-76481 A | 5/2016 |
| WO | WO 2004/039863 A1 | 5/2004 |

(Continued)

OTHER PUBLICATIONS

Delvigs et al., "Addition polyimides from non-mutagenic diamines," High Performance Polymers, vol. 13, pp. 301-312, (2001) (Year: 2001).*

(Continued)

*Primary Examiner* — Ha S Nguyen
(74) *Attorney, Agent, or Firm* — Crowell & Moring LLP

(57) ABSTRACT

A polyimide which is obtained by a reaction of an aromatic diamine having a 1,1,1-trifluoro-2,2-ethanediyl group (—C(CF$_3$)H—), as a linkage skeleton, with a tetracarboxylic dianhydride is easily dissolved in an organic solvent and exhibits excellent film forming properties. In addition, the thus-obtained polyimide can be used for an optical film and a display device.

26 Claims, No Drawings

(56) References Cited

U.S. PATENT DOCUMENTS

| | | | |
|---|---|---|---|
| 8,153,753 | B2 | 4/2012 | Moriyama et al. |
| 10,683,252 | B2 | 6/2020 | Hosoi et al. |
| 10,882,809 | B2 | 1/2021 | Hosoi et al. |
| 11,267,216 | B2 | 3/2022 | Okuyama et al. |
| 2006/0106193 | A1 | 5/2006 | Moriyama et al. |
| 2009/0023886 | A1 | 1/2009 | Saegusa et al. |
| 2010/0234556 | A1 | 9/2010 | Saegusa et al. |
| 2019/0345086 | A1 | 11/2019 | Hosoi et al. |
| 2019/0352246 | A1 | 11/2019 | Hosoi et al. |
| 2020/0180259 | A1 | 6/2020 | Okuyama et al. |
| 2020/0395289 | A1 | 12/2020 | Kim |
| 2022/0106444 | A1 | 4/2022 | Hosoi et al. |
| 2022/0119595 | A1 | 4/2022 | Eguchi et al. |

FOREIGN PATENT DOCUMENTS

| | | | |
|---|---|---|---|
| WO | WO 2016/117237 A1 | 4/2017 | |
| WO | WO 2018/123649 A1 | 7/2018 | |
| WO | WO 2018/139427 A1 | 8/2018 | |
| WO | WO 2019/013182 A1 | 1/2019 | |
| WO | WO 2019/216163 A1 | 11/2019 | |
| WO | 2020/060265 A1 | 3/2020 | |
| WO | WO 2020/162408 A1 | 8/2020 | |
| WO | WO 2020/162411 A1 | 8/2020 | |

OTHER PUBLICATIONS

U.S. Non-Final Office Action issued in U.S. Appl. No. 17/428,762 dated Mar. 6, 2024 (10 pages).
International Search Report (PCT/ISA/210) issued in PCT Application No. PCT/JP2020/003969 dated Apr. 7, 2020 with English translation (four (4) pages).
Japanese-language Written Opinion (PCT/ISA/237) issued in PCT Application No. PCT/JP2020/003969 dated Apr. 7, 2020 (four (4) pages).
Delvigs et al., "Addition Polyimides from Non-Mutagenic Diamines", High Performance Polymers, 2001, pp. 301-312, vol. 13, (12 pages).
Chinese-language Office Action issued in Chinese Application No. 202080013067.2 dated Jan. 12, 2023 (six (6) pages).
International Search Report (PCT/ISA/210) issued in PCT Application No. PCT/JP2020/003964 dated Apr. 14, 2020 with English translation (17 pages).
Japanese-language Written Opinion (PCT/ISA/237) issued in PCT Application No. PCT/JP2020/003964 dated Apr. 14, 2020 (eight (8) pages).
G. K. Surya Prakash et al., "Fluoroanalogs of DDT: Superacidic $BF_3$—$H_2O$ catalyzed facile synthesis of 1, 1, 1,-trifluoro-2, 2-diarylethanes and 1, 1-difluoro-2, 2-diarylethanes.", Organic Letters, 2011, 13(15), 4128-4131. (four (4) pages.
International Search Report (PCT/ISA/210) issued in PCT Application No. PCT/JP2021/025559 dated Sep. 14, 2021 with English translation (four (4) pages).
Japanese-language Written Opinion (PCT/ISA/237) issued in PCT Application No. PCT/JP2021/025559 dated Sep. 14, 2021 (four (4) pages).
Japanese-language Office Action issued in Japanese Application No. 2020-571191 dated Aug. 1, 2023 with English translation (6 pages).
U.S. Final Office Action issued in U.S. Appl. No. 17/428,762 dated Jul. 30, 2024 (6 pages).
Korean-language Office Action issued in Korean Application No. 10-2021-7027909 dated Nov. 14, 2024 (13 pages).
Korean-language Decision of Grant issued in Korean Application No. 10-2021-7027893 dated Feb. 6, 2025 (3 pages).
U.S. Office Action issued in U.S. Appl. No. 17/428,762 dated Mar. 24, 2025 (8 pages).
U.S. Non-Final Office Action issued in U.S. Appl. No. 17/428,762 dated Apr. 22, 2025 (8 pages).

* cited by examiner

POLYAMIDE ACID, POLYIMIDE, OPTICAL FILM, DISPLAY DEVICE AND PRODUCTION METHODS THEREOF

TECHNICAL FIELD

The present disclosure relates to a polyamide acid, a polyimide, an optical film, a display device, and production methods thereof.

BACKGROUND ART

In recent years, there is a demand for thinner, lighter, and more flexible devices in the field of display devices such as organic electroluminescence displays, liquid crystal displays, and electronic papers. An electronic element such as a thin film transistor (TFT) or a transparent electrode is formed on a glass substrate in these devices, and it is possible to reduce the thickness and weight of the devices by changing the glass material to a film material. Transparency is one of the properties required for the film material that can replace glass. Further, since a high temperature process is required to form a fine electronic element made of an inorganic material on a film, an optical film having a high degree of heat resistance is required.

In addition, in an electronic device provided with a display such as a smartphone or a tablet PC, a cover film may be attached to protect the transparent substrate on the display surface. An optical film having light transparency, non-coloring property, and high scratch resistance is required for the cover film.

Polyimide has excellent heat resistance, mechanical properties, and electrical properties. Therefore, polyimide is widely used as a molding material or a composite material in various applications such as electrical/electronic material applications and optical material applications. However, polyimide is usually colored from yellow to brown, and it is difficult to say that the polyimide is suitable for a cover film or a substrate for a display device that requires transparency. The coloring of polyimide is due to a chemical structure thereof, and the formation of a charge transfer complex causes coloring in a visible light region. In order to inhibit the formation of the charge transfer complex, introduction of fluorine into the polyimide, imparting flexibility to a main chain thereof, introduction of a bulky side chain, and the like can be mentioned. For example, Patent Documents 1 and 2 disclose a polyimide into which a hexafluoroisopropanol group (hereinafter, sometimes referred to as an HFIP group) is introduced as a fluorine-containing polyimide.

RELATED DOCUMENT

Patent Document

[Patent Document 1] Japanese Unexamined Patent Publication No. 2016-76480
[Patent Document 2] Japanese Unexamined Patent Publication No. 2016-76481

SUMMARY OF THE INVENTION

Technical Problem

Among monomer raw materials for polymerizing the fluorine-containing polyimide, easily available ones are an aromatic diamine having a hexafluoroisopropylidene group, a tetracarboxylic dianhydride, and an aromatic diamine having a trifluoromethyl group, each of which is represented by the following formulae. However, due to the limited types of these monomers and the limited chemical structure in a case where the monomers are made into a polyimide, there is a problem that it is difficult to achieve excellent transparency and heat resistance while having suitable film forming properties in a case where the polyimide is used as an optical film or a substrate for a display device.

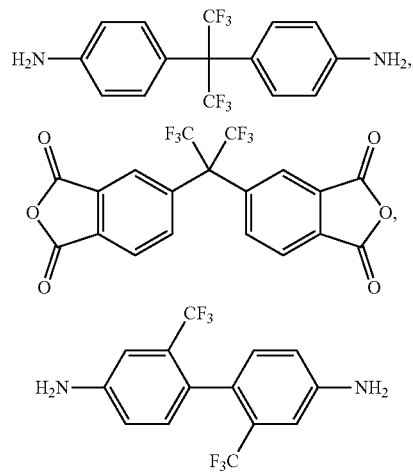

An object of the present disclosure is to provide a polyamide acid and a polyimide, each of which has excellent transparency and heat resistance and excellent film forming processability, an optical film and a display device using the same, and production methods thereof.

Solution to Problem

In view of the foregoing problems, the present inventors have conducted intensive studies. As a result, the present inventors have found that a polyimide obtained by reacting an aromatic diamine having a 1,1,1-trifluoro-2,2-ethanediyl group (hereinafter, sometimes referred to as "(—C(CF$_3$)H—) group") as a linkage skeleton (hereinafter, the linkage skeleton represents a chemical structure of a functional group in which benzene rings containing at least an amino group are linked to each other in an aromatic diamine) with a tetracarboxylic dianhydride is easily dissolved in an organic solvent and has excellent film forming properties, and therefore, an article having improved transparency and heat resistance can be obtained in a case where such a polyimide is used as an optical film and a display device.

In addition, the present inventors have further found that a polyimide having excellent transparency suitable for producing an optical film and a display device can be obtained by using an aromatic amine having a specific substituent on the aromatic ring in addition to the above (—C(CF$_3$)H—) group. The present disclosure has been completed based on these findings.

According to the present disclosure, there is provided a polyimide having a repeating unit represented by General Formula [1] (provided that, excluding a polyimide having a repeating unit represented by General Formula [3] in General Formula [1]).

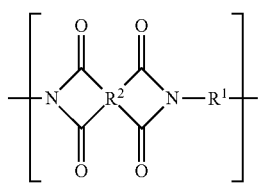

[In General Formula [1], $R^1$ is a divalent organic group represented by General Formula [2], and $R^2$ is a tetravalent organic group:

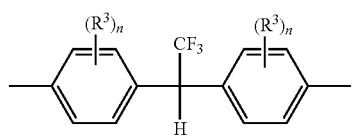

(In General Formula [2], n is an integer of 0 to 4, and $R^3$'s each independently represent a monovalent organic group.)]

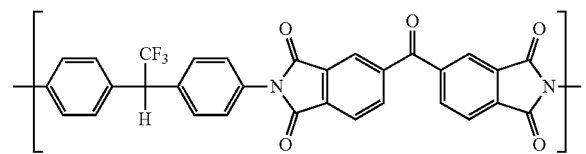

Further, according to the present disclosure, there is provided a polyamide acid having a repeating unit represented by General Formula [1A] (provided that, excluding a polyamide acid having a repeating unit represented by General Formula [3A] in General Formula [1A]).

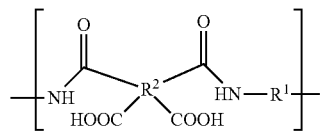

[In General Formula [1A], $R^1$ is a divalent organic group represented by General Formula [2], and $R^2$ is a tetravalent organic group:

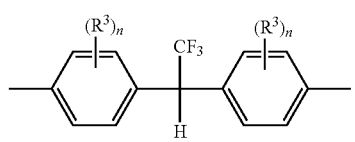

(In General Formula [2], n is an integer of 0 to 4, and $R^3$'s each independently represent a monovalent organic group.)]

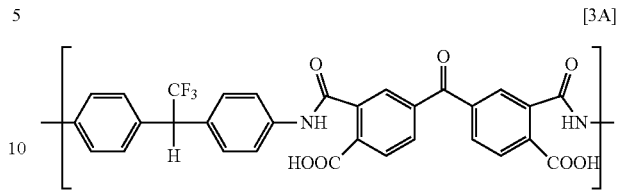

Further, according to the present disclosure, there is provided a polyimide solution including the above-mentioned polyimide and an organic solvent.

Further, according to the present disclosure, there is provided a polyamide acid solution including the above-mentioned polyamide acid and an organic solvent.

Further, according to the present disclosure, there is provided an optical film including the above-mentioned polyimide.

Further, according to the present disclosure, there is provided an optical film including the above-mentioned polyamide acid.

Further, according to the present disclosure, there is provided an optical film including the above-mentioned polyimide and the above-mentioned polyamide acid.

Further, according to the present disclosure, there is provided a display device including the above-mentioned optical film.

Further, according to the present disclosure, there is provided a method for producing a polyimide containing a repeating unit represented by General Formula [1] (provided that, excluding a polyimide having a repeating unit represented by General Formula [3] in General Formula [1]).

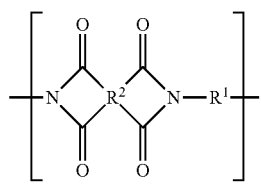

[In General Formula [1], $R^1$ is a divalent organic group represented by General Formula [2], and $R^2$ is a tetravalent organic group:

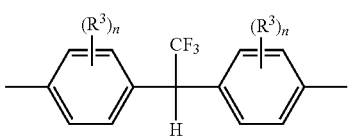

(In General Formula [2], n is an integer of 0 to 4, and $R^3$'s each independently represent a monovalent organic group.)]

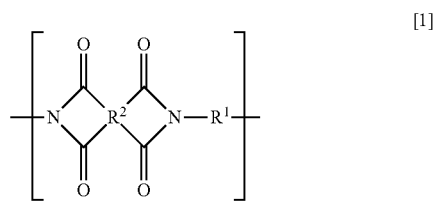

[In General Formula [1], $R^1$ is a divalent organic group represented by General Formula [2], and $R^2$ is a tetravalent organic group:

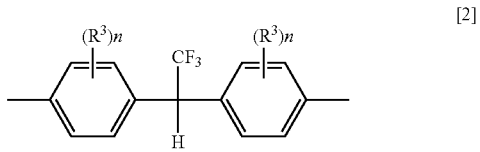

(In General Formula [2], n is an integer of 0 to 4, and $R^3$'s each independently represent a monovalent organic group.)]

However, in the polyimide having the repeating unit represented by General Formula [1] of the present embodiment, the polyimide having the repeating unit represented by General Formula [3] is excluded.

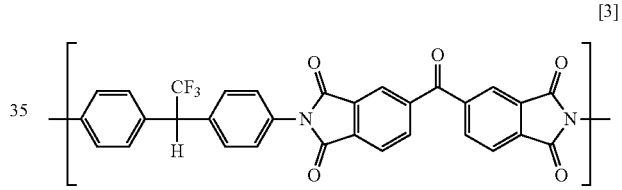

In General Formula [1], the tetravalent organic group according to $R^2$ may contain an organic group selected from the group consisting of an alicyclic group, an aromatic ring, and an alkylene ring. In addition, this $R^2$ may contain a fluorine atom, a chlorine atom, an oxygen atom, a sulfur atom, or a nitrogen atom in a structure thereof. In a case where the structure has a hydrogen atom, a part or all of the hydrogen atom may be substituted with an alkyl group, a fluoroalkyl group, a carboxyl group, a hydroxy group, or a cyano group.

In the divalent organic groups represented by General Formula [2], n is an integer of 0 to 4, and $R^3$'s each independently represent a monovalent organic group. The monovalent organic group is not limited and preferred examples thereof include an alkyl group, an alkoxy group, a cycloalkyl group, an aryl group, an alkenyl group, an alkynyl group, an aryloxy group, an amino group, an alkylamino group, an arylamino group, a cyano group, a nitro group, a silyl group, and a halogeno group (for example, a fluoro group), each of which may have a substituent such as a fluorine atom or a carboxyl group, among which an alkyl group, an alkoxy group, a fluorinated alkyl group (for example, a trifluoromethyl group), a halogeno group (for example, a fluoro group), and a nitro group are more preferable. The alkyl group as $R^3$ is not limited, but is preferably a linear or branched alkyl group having 1 to 6 carbon atoms, among which an n-butyl group, an s-butyl group, an isobutyl group, a t-butyl group, an n-propyl group,

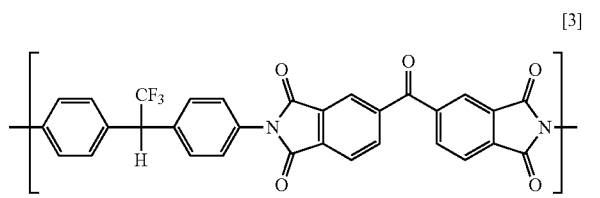

the method including a step of polycondensing a diamine represented by General Formula [2A]:

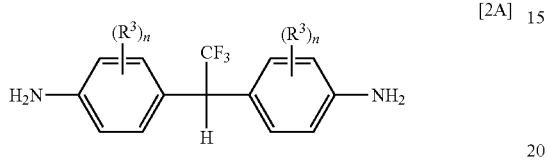

[in General Formula [2A], $R^3$'s each independently represent a monovalent organic group, and n represents 0 to 4.]

with a tetracarboxylic dianhydride represented by General Formula [4]:

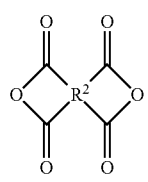

[in General Formula [4], $R^2$ is a tetravalent organic group.]

to obtain the polyimide having a repeating unit represented by General Formula [1].

Furthermore, according to the present disclosure, there is provided a method for producing an optical film or a display device, including:

a step of applying the polyimide solution or the polyamide acid solution to a supporting base material;

a step of removing a solvent contained in the polyimide solution or the polyamide acid solution, followed by drying to produce a resin film containing polyimide or polyamide; and a step of heat-treating and curing the resin film.

Advantageous Effects of Invention

According to the present disclosure, a polyimide or polyamide acid having excellent transparency, heat resistance, and film forming processability is provided by a reaction of an aromatic diamine having a —C(CF$_3$)H— group with a tetracarboxylic dianhydride.

DESCRIPTION OF EMBODIMENTS

Hereinafter, embodiments of the present disclosure will be described in more detail, but the present disclosure is not limited thereto.

[Polyimide]

The polyimide of the present embodiment has a repeating unit represented by General Formula [1].

an i-propyl group, an ethyl group, and a methyl group are preferable, and an ethyl group and a methyl group are particularly preferable. On the other hand, the alkoxy group as $R^3$ is not limited, but is preferably a linear or branched alkoxy group having 1 to 6 carbon atoms, among which an n-butoxy group, an s-butoxy group, an isobutoxy group, a t-butoxy group, an n-propoxy group, an i-propoxy group, an ethoxy group, and a methoxy group are preferable, and an ethoxy group and a methoxy group are particularly preferable. In addition, the alkyl group or alkoxy group may be one in which, for example, a halogen atom, an alkoxy group, and a haloalkoxy group are substituted on any carbon thereof in any number and in any combination. Furthermore, in a case where the number of $R^3$'s in the aryl compound is 2 or more, these 2 or more $R^3$'s may be linked to form a saturated or unsaturated monocyclic or polycyclic cyclic group having 3 to 10 carbon atoms. The number (n) of $R^3$'s bonded in General Formula [2] is an integer of 0 to (5-m) and preferably an integer of 0 to 2.

In one embodiment, in a case where the type of $R^3$ is an alkyl group among the monovalent organic groups, it is preferably a linear or branched alkyl group having 1 to 6 carbon atoms, among which an n-butyl group, an s-butyl group, an isobutyl group, a t-butyl group, an n-propyl group, an i-propyl group, an ethyl group, and a methyl group are preferable, and an ethyl group and a methyl group are particularly preferable.

As an example of the divalent organic group represented by General Formula [2], any of the following divalent organic groups can be mentioned.

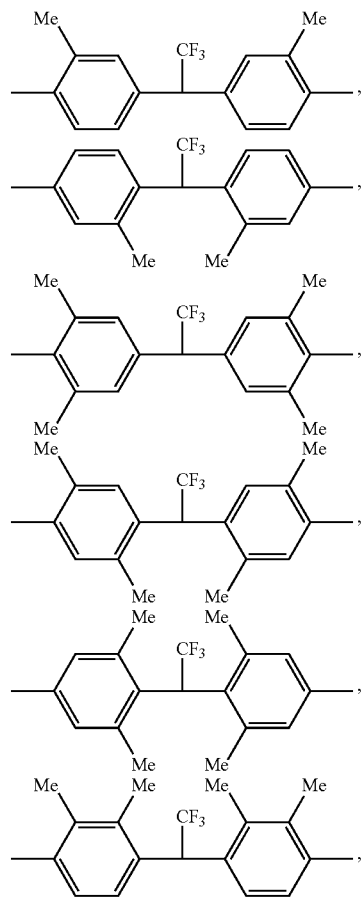

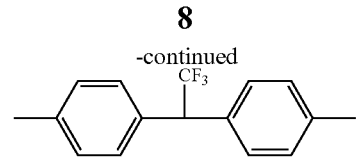

The $R^2$ is preferably any of the following tetravalent organic groups.

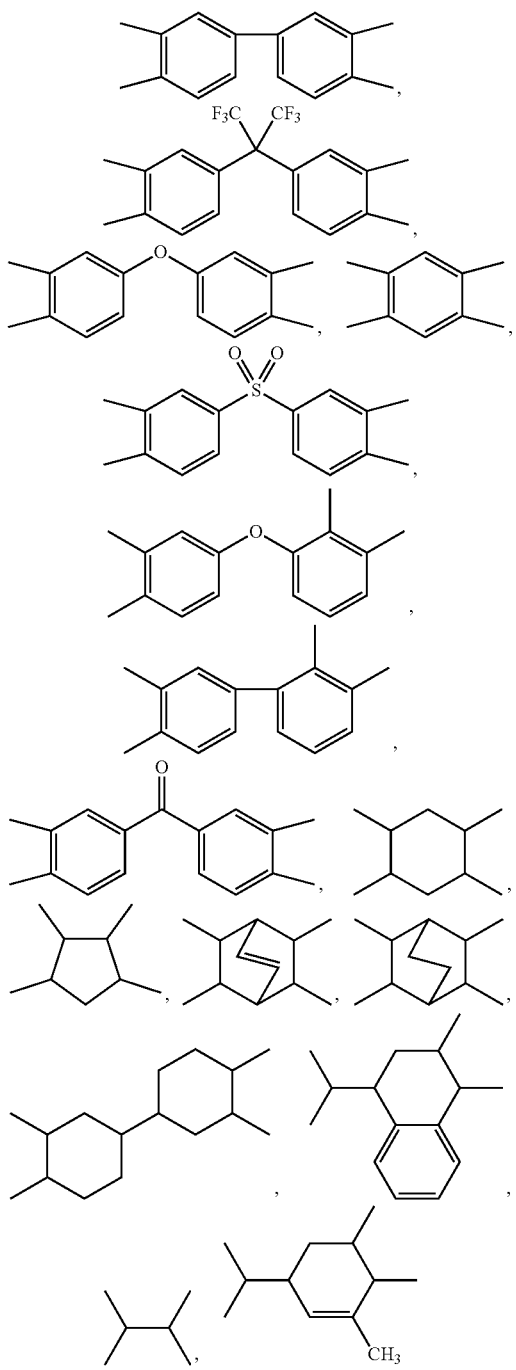

The polyimide of the present embodiment having the repeating unit represented by General Formula [1] is particularly preferably a polyimide having a structural unit represented by any of the following formulae.

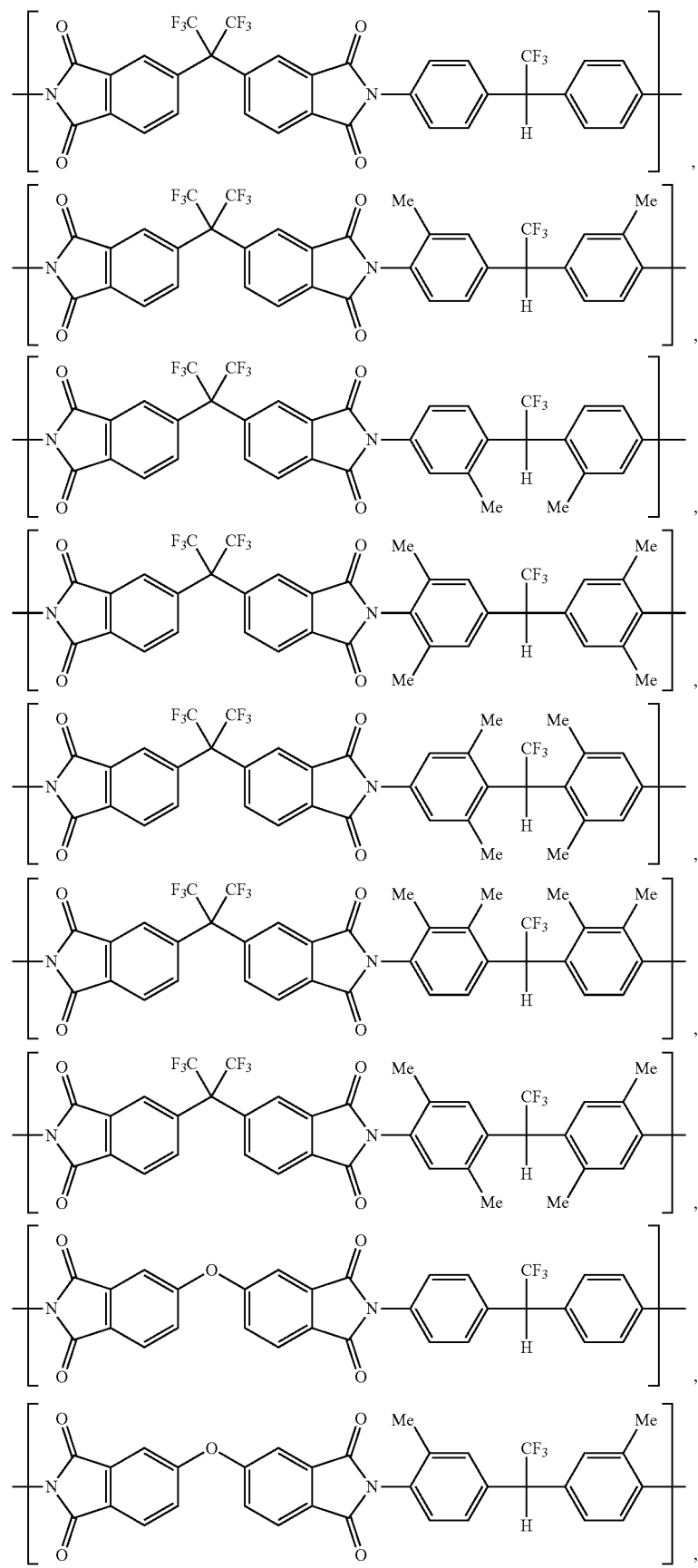

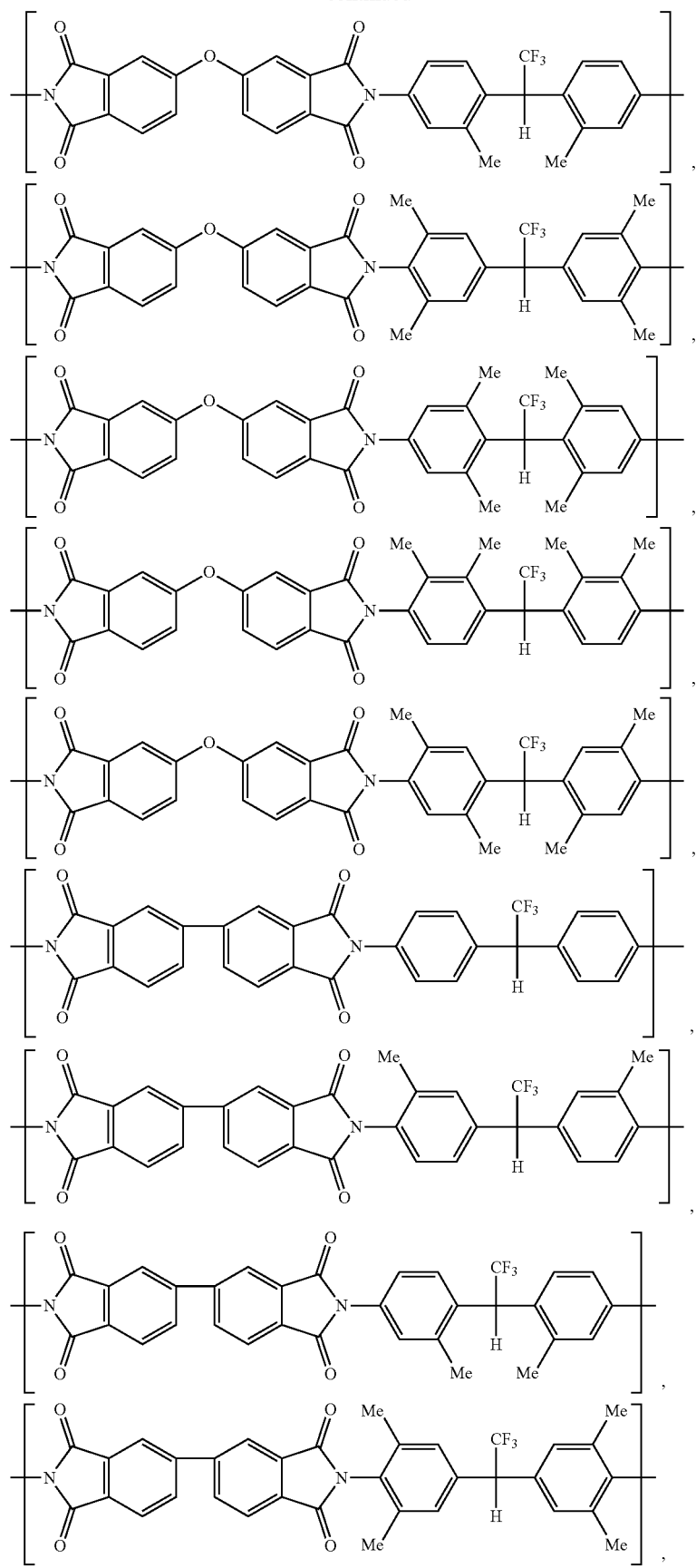

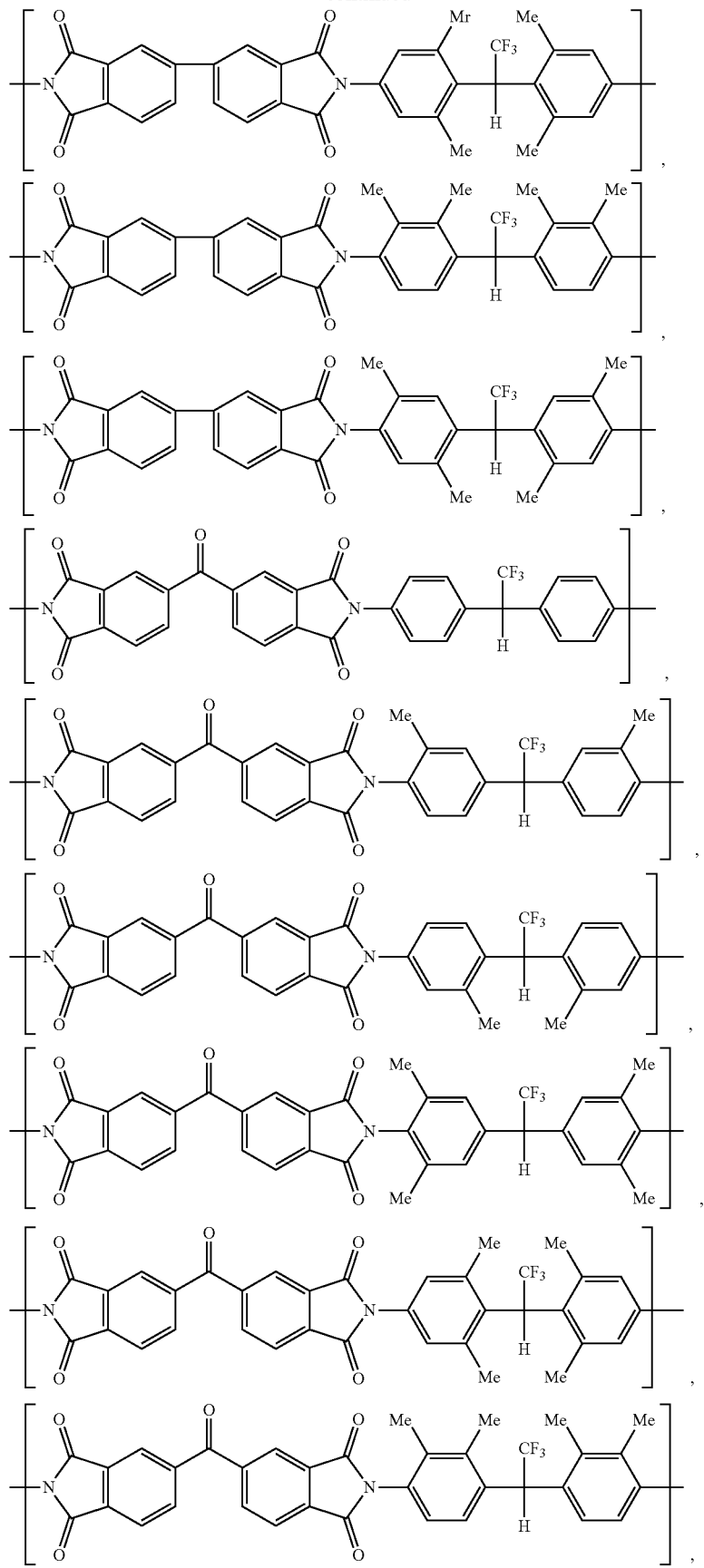

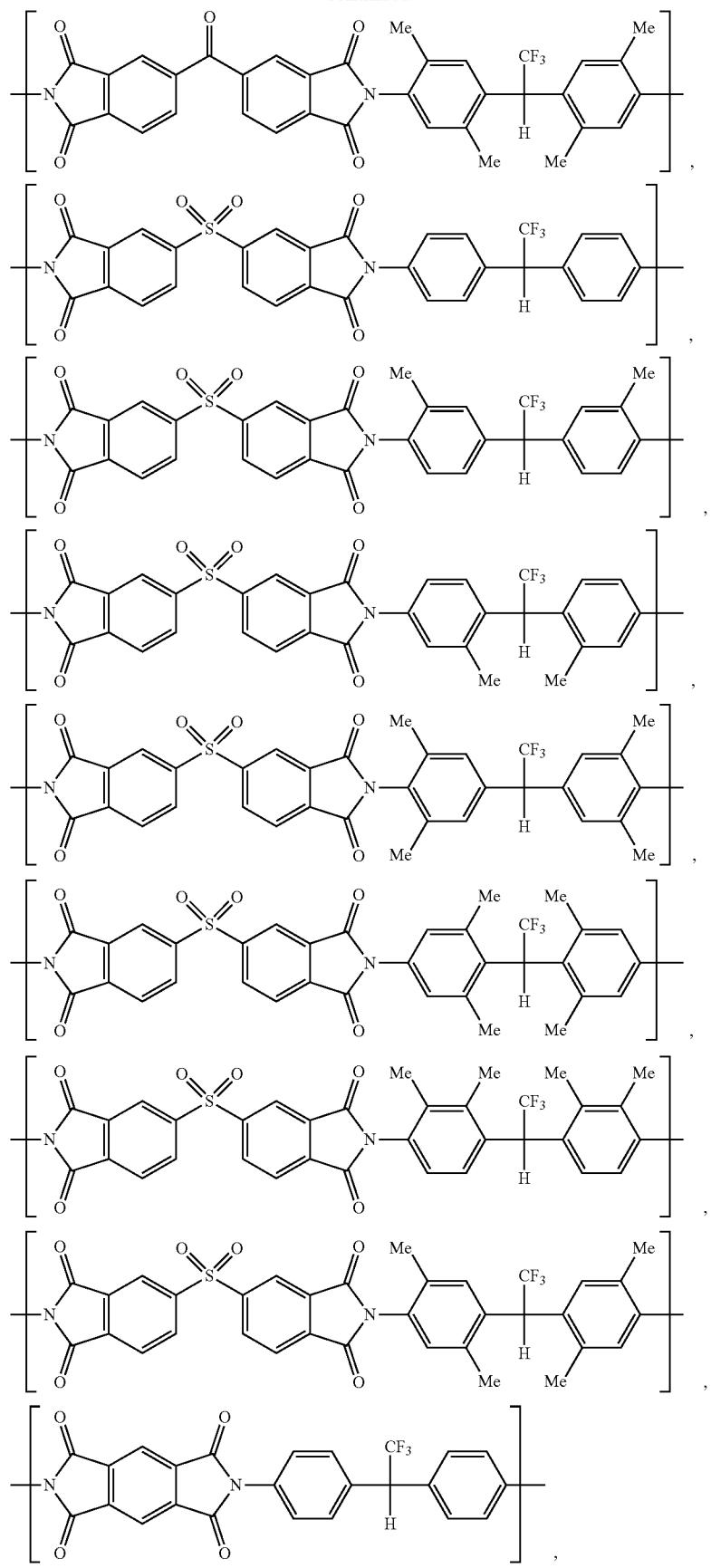

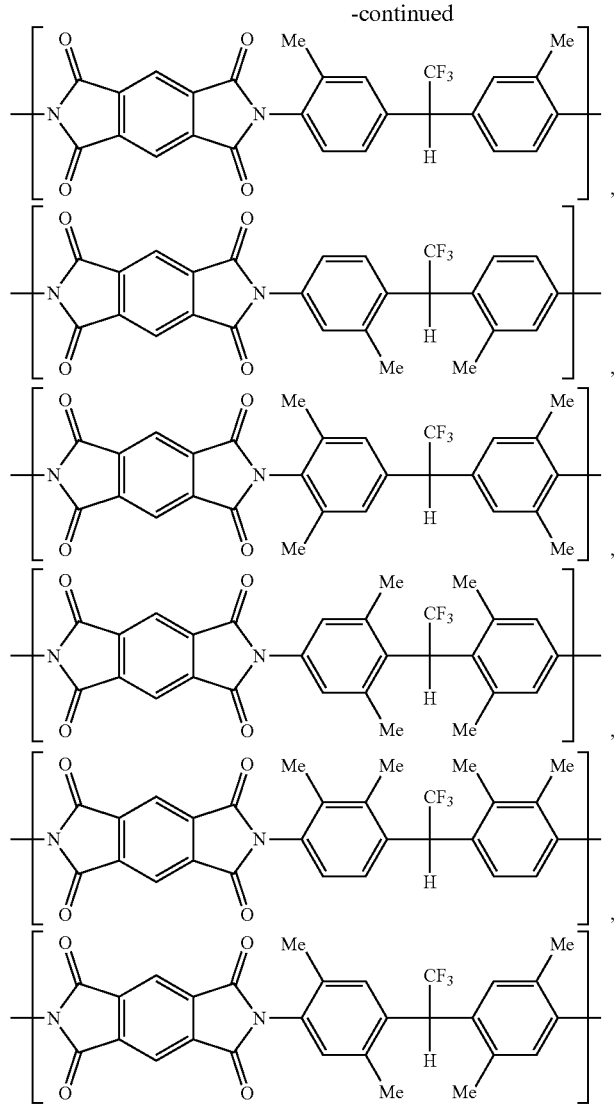

In the polyimide of the present embodiment, the weight average molecular weight thereof is not particularly limited. However, in a case where the polyimide is used as an optical film and a substrate for a display device, the weight average molecular weight of the polyimide is equal to or more than 1,000 and equal to or less than 1,000,000, and particularly preferably equal to or more than 30,000 and equal to or less than 200,000. Ina case where the weight average molecular weight of the polyimide is less than 1,000 or in a case where the weight average molecular weight of the polyimide is more than 1,000,000, it may affect the performance of the polyimide as a substrate and the state of film formation of the polyimide on the base material. In the present specification, the weight average molecular weight is a value obtained by measuring a sample with gel permeation chromatography (hereinafter, sometimes referred to as "GPC") and calculating the measured value in terms of polystyrene using a standard polystyrene calibration curve.

[Polyamide Acid]

The polyamide acid (polyamic acid) of the present embodiment has a repeating unit represented by General Formula [1A].

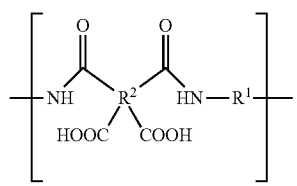

[1A]

[In General Formula [1A], $R^1$ is a divalent organic group represented by General Formula [2], and $R^2$ is a tetravalent organic group:

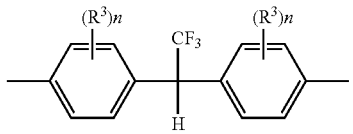

[2]

(In General Formula [2], n is an integer of 0 to 4 and $R^3$'s each independently represent a monovalent organic group.)]

However, in the polyamide acid having the repeating unit represented by General Formula [1A] of the present embodiment, the polyamide acid having the repeating unit represented by General Formula [3A] is excluded.

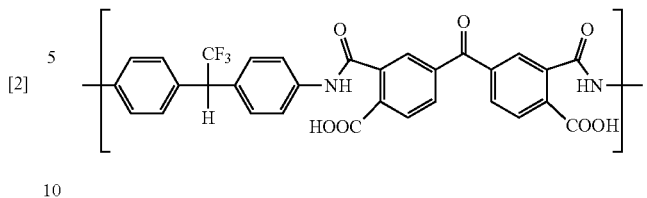

$R^1$ and $R^2$ in General Formula [1A] have the same definition as that of $R^1$ and $R^2$ of the polyimide containing the repeating unit represented by General Formula [1], and thus the description thereof will not be repeated.

The polyamide acid of the present embodiment having the repeating unit represented by General Formula [1A] is particularly preferably a polyamide acid having a structural unit represented by any of the following formulae.

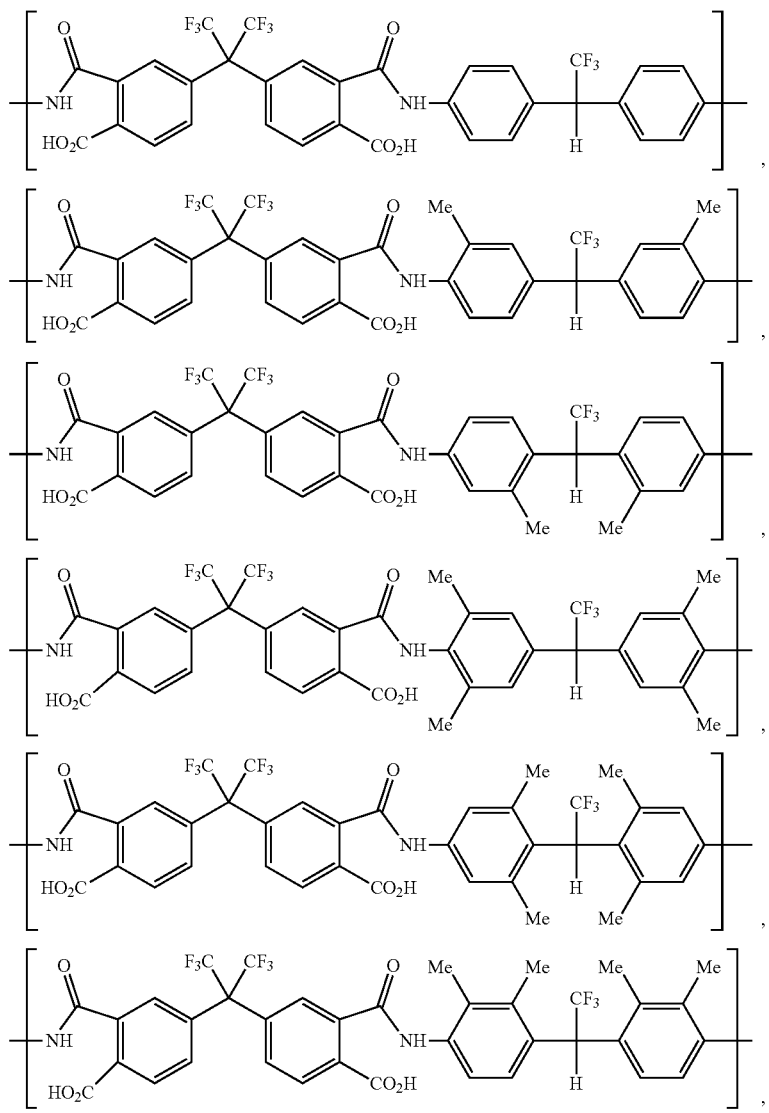

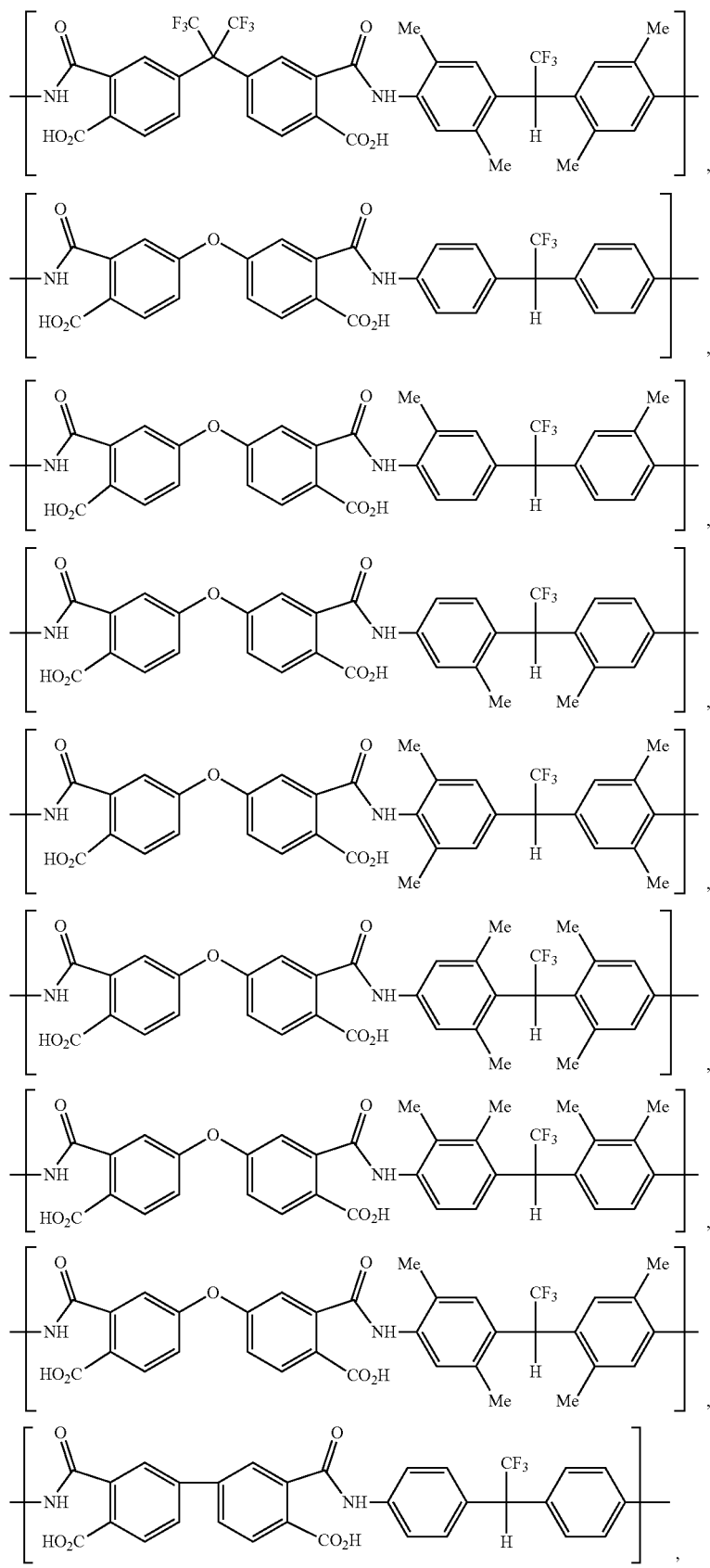

-continued
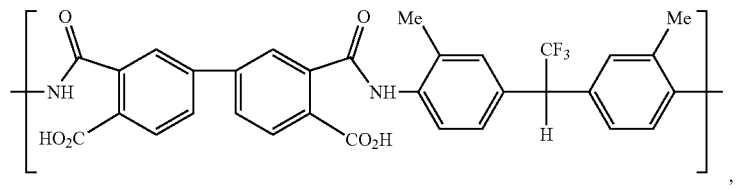,
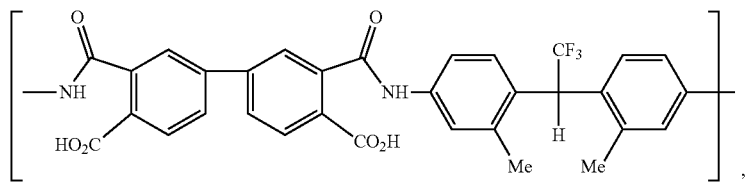,
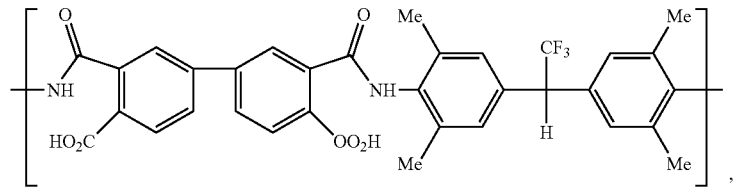,
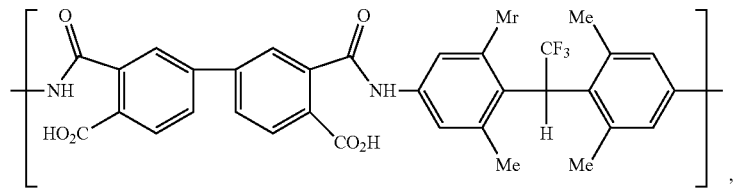,
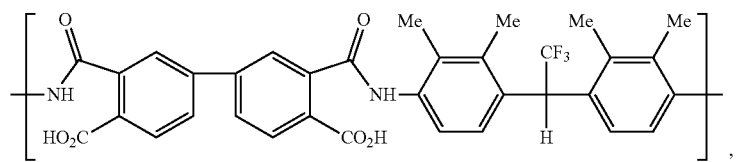,
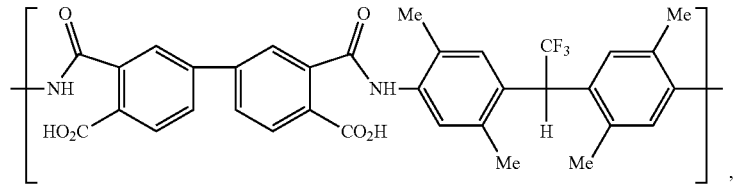,
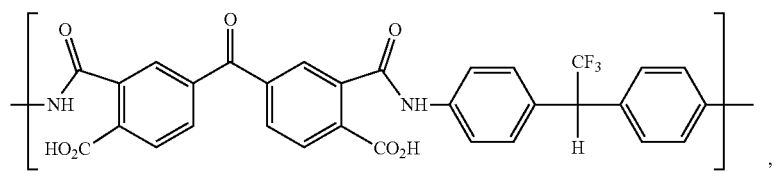,
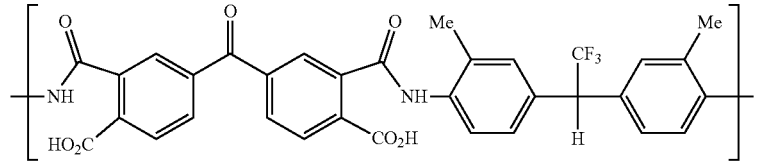,
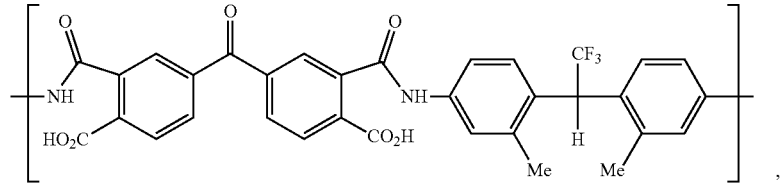, -continued
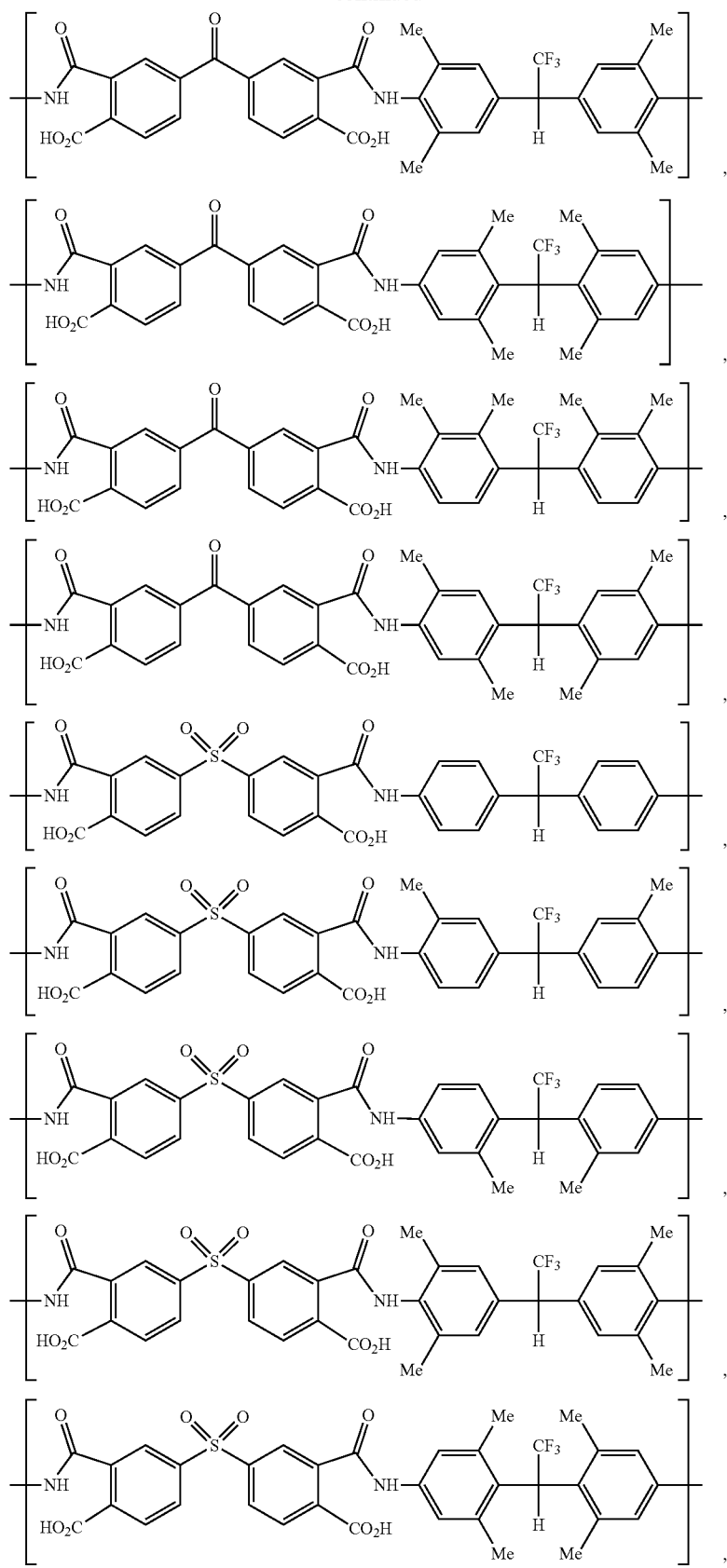

-continued

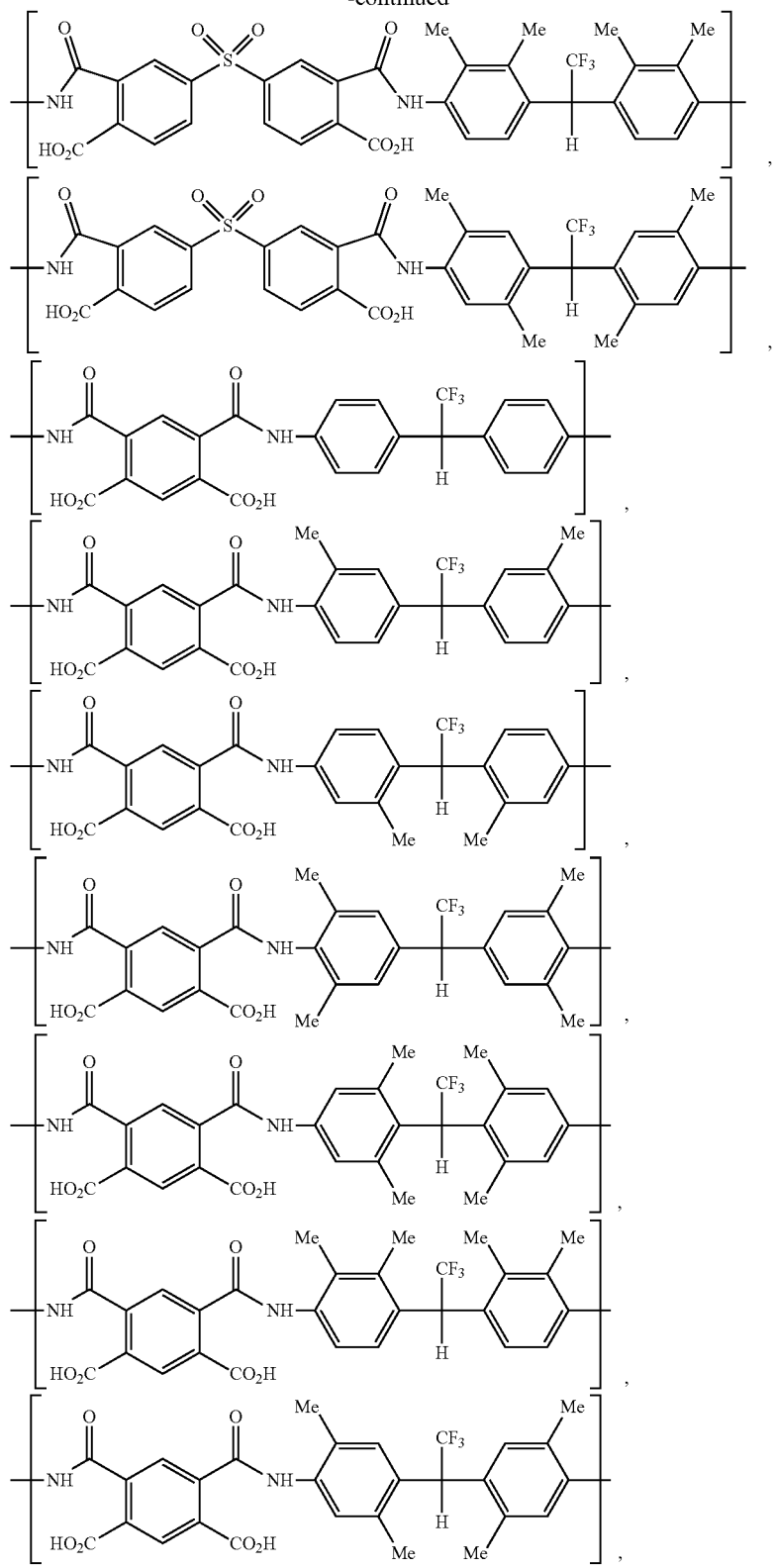

In the polyamide acid according to the present embodiment, the weight average molecular weight thereof is not particularly limited. However, in a case where the polyamide acid is used as an optical film and a substrate for a display device, the weight average molecular weight of the polyamide acid is equal to or more than 1,000 and equal to or less than 1,000,000, and particularly preferably equal to or more than 30,000 and equal to or less than 500,000. In a case where the weight average molecular weight of the polyamide acid is less than 1,000 or in a case where the weight average molecular weight of the polyamide acid is more than 1,000,000, it may affect the performance of the polyimide as a substrate and the state of film formation of the polyimide on the base material. In addition, in the present specification, The polyamide acid and the polyimide according to the present embodiment may be used alone or may be used in admixture of the polyimide and the polyamide acid.

[Production Method of Polyamide Acid and Polyimide]

The method for producing the polyamide acid (Formula [1A] above) and the polyimide (Formula [1] above) according to the present embodiment is not particularly limited and may be, for example, a production method by a reaction of a diamine represented by General Formula [2A] with a tetracarboxylic dianhydride represented by General Formula [4]. Examples of the production method include a method in which the diamine and the tetracarboxylic dianhydride are mutually melted at equal to or higher than 150° C. Another example of the production method is a method for producing the polyimide according to the present embodiment (Formula [1] above) by dehydrating and ring-closing the polyamide acid (Formula [1A] above) obtained by polycondensing these raw material compounds in an organic solvent. This polycondensation reaction is preferably carried out at −20° C. to 80° C., and the diamine and the tetracarboxylic dianhydride are preferably reacted in a molar ratio of 1:1.

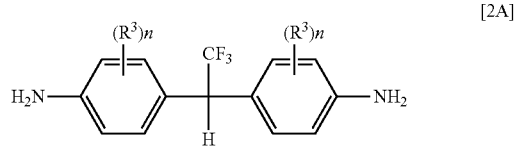

[2A]

In General Formula [2A], $R^3$'s each independently represent a monovalent organic group, and n represents 0 to 4.

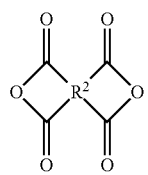

[4]

In General Formula [4], $R^2$ has the same definition as $R^2$ in General Formula [1].

$R^3$ in the diamine represented by General Formula [2A] has the same definition as $R^3$ in the divalent organic group represented by General Formula [2]. The type of $R^3$ is not limited, but for example, in a case where $R^3$ is an alkyl group, it is preferably a linear or branched alkyl group having 1 to 6 carbon atoms, among which an n-butyl group, an s-butyl group, an isobutyl group, a t-butyl group, an n-propyl group, an i-propyl group, an ethyl group, and a methyl group are preferable, and an ethyl group and a methyl group are particularly preferable.

As examples of the diamine represented by General Formula [2A] in a case where $R^3$ is a methyl group, diamines having the following structure can be mentioned.

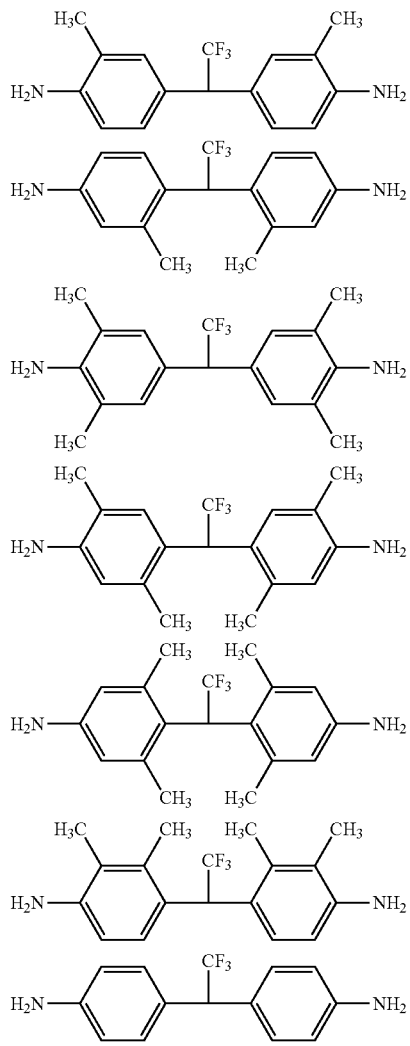

The tetracarboxylic dianhydride represented by General Formula [4] is particularly preferably any of the following.

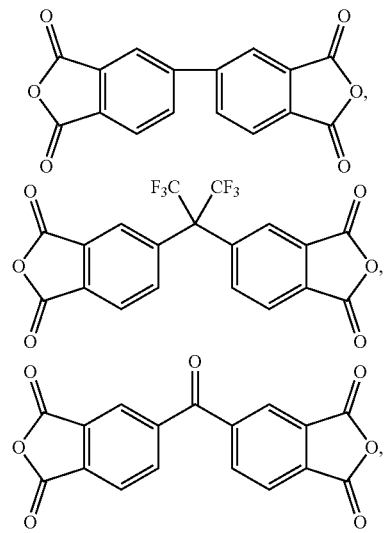

-continued

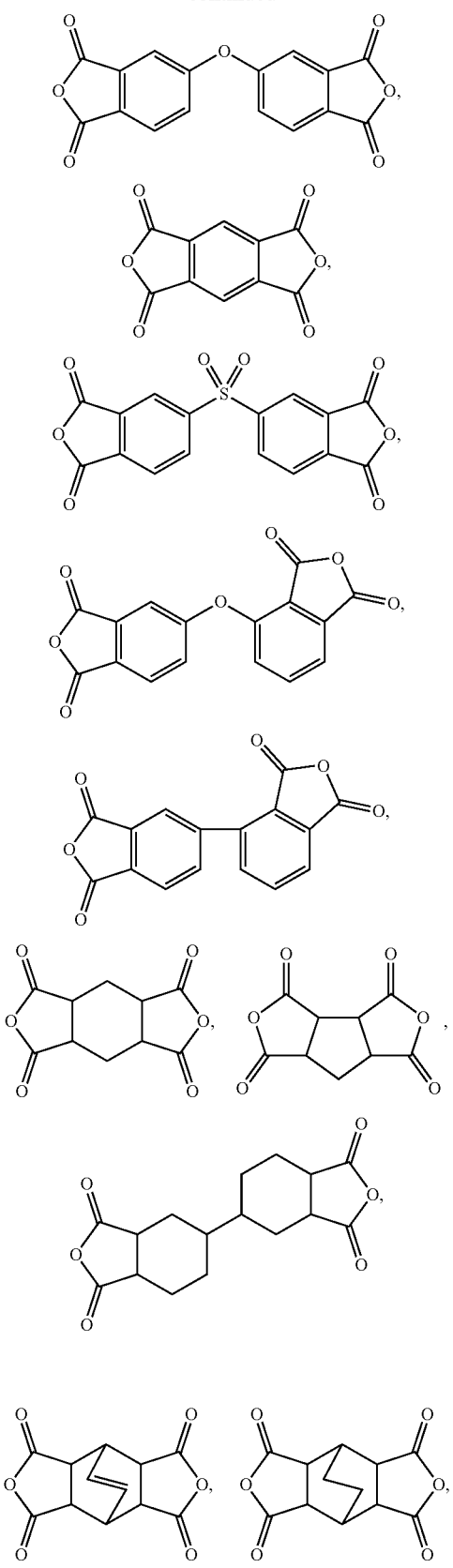

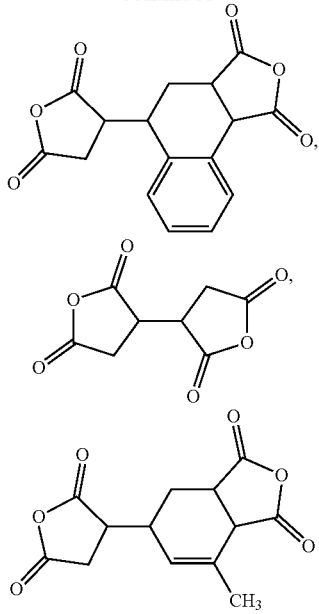

Examples of other diamine compounds that can be used in combination include o-phenylenediamine, m-phenylenediamine, p-phenylenediamine, 2,4-diaminotoluene, 2,5-diaminotoluene, 4-diamino-m-xylene, 2,4-diaminoxylene, 2,2-bis(4-(4-aminophenyl) hexafluoropropane, and 2,2'-bis(trifluoromethyl)benzidine, from the viewpoint of availability. 2,2-bis(4-(4-aminophenyl)hexafluoropropane), which has less decrease in transparency, is particularly preferable. These compounds may be used alone or in combination of two or more thereof.

The organic solvent that can be used in the polycondensation reaction is not particularly limited as long as the raw material compound is dissolved therein, and examples thereof include an amide-based, an ether-based solvent, an aromatic hydrocarbon-based solvent, a halogen-based solvent, and a lactone-based solvent. Specific examples of the organic solvent include N,N-dimethylformamide, N,N-dimethylacetamide (DMAc), N-methylformamide, hexamethyl phosphoric acid triamide, N-methyl-2-pyrrolidone, diethyl ether, dipropyl ether, diisopropyl ether, dibutyl ether, cyclopentyl methyl ether, diphenyl ether, dimethoxyethane, diethoxyethane, tetrahydrofuran, dioxane, trioxane, benzene, anisole, nitrobenzene, benzonitrile, chloroform, dichloromethane, 1,2-dichloroethane, 1,1,2,2-tetrachloroethane, γ-butyrolactone, γ-valerolactone, ε-valerolactone, γ-caprolactone, ε-caprolactone, and α-methyl-γ-butyrolactone. These organic solvents may be used alone or in combination of two or more thereof.

The polyimide according to the present embodiment (Formula [1] above) can be obtained by further dehydrating and ring-closing the polyamide acid (Formula [1A] above) obtained by the polycondensation reaction to be imidized. This dehydration ring closure reaction is carried out under conditions of a heating method, chemical method, or the like that promote cyclization. A solution of the polyimide according to the present embodiment can be obtained by the heating method in which the polyamide acid immediately after polymerization is imidized by heating at a high temperature of 150° C. to 350° C., or by the chemical method in which a base such as pyridine or triethylamine and an acetic anhydride are each added in an amount of equal to or more than 0.1 molar equivalents and less than 10 equivalents at room temperature (0° C. to 50° C.) to a raw material diamine to be imidized. The concentration of the polyimide in this solution is preferably equal to or more than 5% by mass and equal to or less than 50% by mass. In a case where the concentration of the polyimide is less than 5% by mass, practicality and efficiency may be affected, and in a case where the concentration of the polyimide is greater than 50% by mass, solubility may be affected. Further, the concentration of the polyimide is preferably equal to or more than 10% by mass and equal to or less than 40% by mass.

The solution of the polyimide and the polyamide acid according to the embodiment can be used as it is in the production of the optical film of the present embodiment. In addition, for the purpose of removing residual monomers and low molecular weight substances contained in the solution of the polyimide and the polyamide acid according to the present embodiment, the solution of the polyimide and the polyamide acid according to the present embodiment may be added to a poor solvent such as water or alcohol to precipitate, isolate and purify the polyimide and the polyamide acid. Then, the purified polyimide and polyamide acid may be adjusted while being dissolved again in an organic solvent to the above concentration, and the adjusted solution may be used for producing the optical film of the present embodiment. The organic solvent is not particularly limited as long as the polyimide and the polyamide acid according to the present embodiment are dissolved therein. Examples of the organic solvent include organic solvents of the same type as those mentioned in the organic solvents that can be used for the polycondensation reaction, which may be used alone or may be used as a mixed solvent of two or more thereof.

[Method for Producing Optical Film]

An optical film and a substrate for a display device, each of which contains the above-mentioned polyimide, can be obtained by heat-treating the above-mentioned solution of the polyimide and the polyamide acid. Specifically, the optical film and the substrate can be obtained through a step of applying the solution of the polyimide and the polyamide acid according to the present embodiment to a supporting base material (coating step), a step of removing a solvent, followed by drying (solvent removing step), and a step of further heat-treating the obtained resin film (heating step).

The coating method used in the coating step is not particularly limited, and a known method can be adopted. A known coating device such as a spin coater, a bar coater, a doctor blade coater, an air knife coater, a roll coater, a rotary coater, a flow coater, a die coater, or a lip coater can be appropriately used according to a desired coating thickness, resin viscosity, or the like.

The supporting base material is not particularly limited, but an inorganic base material or an organic base material is suitable. Specific examples of the supporting base material include glass, silicon wafer, stainless steel, alumina, copper, nickel, polyethylene terephthalate, polyethylene glycol terephthalate, polyethylene glycol naphthalate, polycarbonate, polyimide, polyamide imide, polyether imide, polyether ether ketone, polypropylene, polyether sulfone, polyethylene terephthalate, polyphenylene sulfone, and polyphenylene sulfide.

Above all, from the viewpoint of heat resistance, it is favorable to use an inorganic base material, and it is preferable to use an inorganic base material such as glass, silicon wafer, or stainless steel. In a case of being applied to the supporting base material, the thickness of the film according to the present embodiment can be appropriately adjusted by the concentration of the resin component in the solution of the polyimide and the polyamide acid according to the present embodiment, and is usually equal to or more than 1 μm and equal to or less than 1,000 μm and preferably equal to or more than 5 μm and equal to or less than 500 μm. In a case where the coating film is thinner than 1 μm, it is difficult to obtain sufficient strength for the molded substrate. In a case where the coating film is thicker than 1,000 μm, defects such as cissing, dents, and cracks of the substrate occur, which makes it difficult to obtain a uniform substrate.

After obtaining a coating film by the coating step, an optical film is obtained by further carrying out a solvent removing step of removing the solvent from the coating film and drying the coating film and a heating step of heat-treating and curing the dried coating film (resin film).

The temperature at which the solvent is removed and the coating film is dried in the solvent removing step also depends on the type of the organic solvent in which the polyimide and the polyamide acid according to the present embodiment are dissolved, but is preferably equal to or higher than 50° C. and equal to or lower than 250° C. and more preferably equal to or higher than 80° C. and equal to or lower than 200° C. In a case where the temperature in the solvent removing step is lower than 50° C., drying will be insufficient. In a case where the temperature in the solvent removing step is higher than 250° C., rapid solvent evaporation will occur, which may cause defects such as cissing, dents, and cracks, and may cause the formation of a non-uniform film.

In the heating step after the solvent removing step, the resin film can be cured by a heat treatment at a high temperature to obtain the optical film of the present embodiment. In this step, it is expected that the residual solvent that could not be removed in the solvent removing step can be removed, the imidization ratio can be improved, and the physical properties can be improved. In the heating step, the temperature at which the resin film is heat-treated and cured is preferably equal to or higher than 150° C. and equal to or lower than 400° C. and more preferably equal to or higher than 200° C. and equal to or lower than 300° C. In a case where the temperature in the heating step is lower than 150° C., a sufficient imidization ratio may not be obtained. In a case where the temperature in the heating step is higher than 400° C., this causes defects such as cracks in the obtained substrate.

The heating step is preferably carried out using an inert gas oven, a hot plate, a box dryer, or a conveyor dryer, but is not limited to the use of these devices. The heating step is preferably carried out under an inert gas stream from the viewpoint of preventing oxidation of the resin film and removing the solvent. Examples of the inert gas include nitrogen and argon. The flow rate of the inert gas is preferably equal to or more than 1 L/min and equal to or less than 5 L/min. In a case where the flow rate of the inert gas is slower than 1 L/min, solvent removal and curing of the resin film may be insufficient. In a case where the flow rate of the inert gas is faster than 5 L/min, only the surface of the resin film dries, which may cause cracks and the like.

Depending on the intended use and purpose, in order to obtain a substrate containing the polyimide of the present embodiment (hereinafter, sometimes referred to as a polyimide substrate), a peeling step of peeling the polyimide film from the supporting base material after the heating step and using the polyimide film as the polyimide substrate is required. The peeling step can be carried out after cooling from room temperature (20° C.) to about 400° C. after the heating step. At this time, in order to easily carry out the peeling, a peeling agent may be applied to the supporting base material. The peeling agent at that time is not particularly limited, and examples thereof include a silicon-based or fluorine-based peeling agent.

[Performance of Optical Film and Display Device]

Hereinafter, the physical properties and characteristics of the polyimide related to the optical film and the display device of the present embodiment will be described.

The polyimide having a (—C(CF$_3$)H—) group of the present embodiment has moldability, and excellent transparency and heat resistance. Furthermore, the polyimide containing a methyl group in addition to the (—C(CF$_3$)H—) group exhibits even better transparency.

In addition, since the (—C(CF$_3$)H—) group has an asymmetric structure, the polyimide has high solubility in a specific organic solvent, thus making it easy to prepare a polyimide solution, and can be molded into a desired film shape.

Further, the polyimide having a (—C(CF$_3$)H—) group of the present embodiment can contain a (—C(CF$_3$) H—) group in an aromatic diamine as a raw material, and thus has high flexibility and excellent mechanical strength as compared with the conventional polyimide containing fluorine-containing polyimide. This makes it possible to design a structure for improving the film strength.

<Transparency>

Regarding the transparency of the optical film and the substrate for a display device of the present embodiment, the light transmittance at a wavelength of 400 nm to 780 nm is preferably equal to or more than 50% and more preferably equal to or more than 70% at a film thickness of 20 μm to 70 μm.

<Heat Resistance>

The heat resistance of the optical film and the substrate for a display device of the present embodiment is indexed by a glass transition temperature (hereinafter, sometimes referred to as Tg) and a 5% weight loss temperature (hereinafter, sometimes referred to as Td$_5$). The Tg is preferably equal to or higher than 280° C. from the viewpoint of heat resistance and is more preferably equal to or higher than 300° C. from the viewpoint of being able to cope with a high process temperature. The Td$_5$ is preferably equal to or higher than 300° C. and more preferably equal to or higher than 350° C. In a case where the Td$_5$ is lower than 300° C., this causes deterioration of the substrate in the device preparation process.

EXAMPLES

Hereinafter, the present disclosure will be described in more detail with reference to Examples, but the present disclosure is not limited thereto.

The identification and physical properties evaluation of the polymer compounds obtained in the present Examples were carried out by the methods shown below.

[Weight Average Molecular Weight (Mw) and Number Average Molecular Weight (Mn)]

The weight average molecular weight and the number average molecular weight were measured using gel permeation chromatography (GPC, HLC-8320 manufactured by Tosoh Corporation). Tetrahydrofuran (THF) was used as a mobile phase, and TSKgel SuperHZM-H was used as a column. Alternatively, N,N-dimethylformamide, 30 mmol/L lithium bromide, or 60 mmol/L phosphoric acid was used as the mobile phase, and TSKgel α-M or TSKgel α-2500 was used as the column.

[Infrared Absorption Spectrum (IR) Measurement]

The infrared absorption spectrum of the compound or the compound film was measured using Nicolet NEXUS 470 FT-IR (manufactured by Thermo Fisher Scientific Inc.).

[Transparency]

For the transparency, a light transmittance at a wavelength of 400 nm (T400) was measured using the polyimide optical films obtained in Examples and Comparative Examples and using an ultraviolet-visible-near-infrared spectrometer (Model: UV-VIS-NIR SPECTROMETER UV-3150, manufactured by Shimadzu Corporation).

[Heat Resistance]

The heat resistance was evaluated by measuring the glass transition temperature and the 5% weight loss temperature (Td$_5$). The glass transition temperature (Tg) is a temperature, as measured with a differential scanning calorimeter (Model: DSC 7000, manufactured by Hitachi High-Tech Science Corporation), at which the differential scanning calorimetry is carried out under the conditions that the temperature is raised to 400° C. at a temperature rising rate of 10° C./min, lowered to −40° C. at a temperature lowering rate of −10° C./min, and raised again to 400° C. at a temperature rising rate of 10° C./min and then the change in differential scanning calory at the time of the second temperature rise becomes maximum. The 5% weight loss temperature (Td$_5$) is a temperature at which thermogravimetric measurement is carried out under the condition of a temperature rising rate of 10° C./min using a simultaneous differential thermogravimetric analyzer (Model: STA 7200, manufactured by Hitachi High-Tech Science Corporation) and then there is a weight loss of 5% with respect to the initial weight.

Synthesis Example 1 of Diamine (Synthesis of BIS-A-EF)

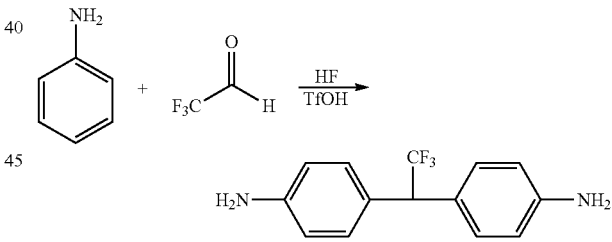

5.3 g (fluoral: 30 mmol, hydrogen fluoride: 0.12 mol) of the fluoral-containing mixture (hydrogen fluoride: 44% by weight, hydrogen chloride: 1% by weight, organic matter: 55% by weight) prepared with reference to Japanese Unexamined Patent Publication No. 2018-115146, 9.6 g (0.48 mol) of hydrogen fluoride, 5.6 g (60 mmol) of aniline, and 2.3 g (15 mmol) of trifluoromethanesulfonic acid were weighed in a 100 mL stainless steel autoclave reactor equipped with a pressure gauge, a thermometer protection tube, an insertion tube, and a stirring motor, heated in an oil bath at 150° C., and reacted at an absolute pressure of 1.3 MPa for 5 hours. The reaction solution was poured into 100 g of ice, 70 g of a 48% potassium hydroxide aqueous solution was added thereto for neutralization, and an organic matter was extracted with 100 g of ethyl acetate. In a case where the extracted organic layer was analyzed by gas chromatography, the conversion rate of aniline was 96%. The organic layer recovered by the extraction operation was washed with 50 g of water and further washed with 50 g of saturated sodium bicarbonate water, and then the organic layer was recovered by the liquid separation operation. The organic layer was concentrated with an evaporator to obtain a target product 1,1,1-trifluoro-2,2-bis (4-aminophenyl)ethane (sometimes referred to as "BIS-A-EF") in a yield of 93% and an isomer ratio of 92/8 (2,2-bis(4-aminophenyl) form/unidentified).

[Physical Properties Data]

1,1,1-trifluoro-2,2-bis(4-aminophenyl)ethane $^1$H-NMR (400 MHz, CDCl$_3$) δ (ppm): 3.42 (4H, s), 4.45 (1H, q, J=10.1 Hz), 6.62 (4H, d, J=8.3 Hz), 7.12 (4H, d, J=8.3 Hz)
$^{19}$F-NMR (400 MHz, CDCl$_3$, CFCl$_3$) δ (ppm): −66.9 (3F, d, J=11.5 Hz)

Synthesis Example 2 of Diamine (Synthesis of BIS-3-AT-EF)

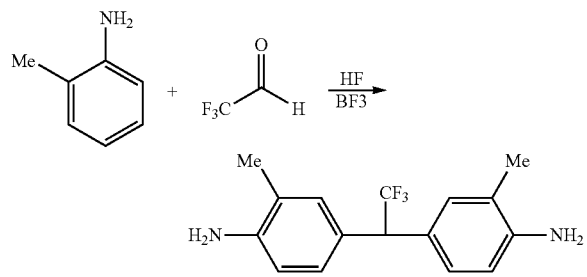

15.9 g (fluoral: 90 mmol, hydrogen fluoride: 0.36 mol) of the fluoral-containing mixture (hydrogen fluoride: 44% by weight, hydrogen chloride: 1% by weight, organic matter: 55% by weight) prepared with reference to Japanese Unexamined Patent Publication No. 2018-115146, 28.8 g (1.44 mol) of hydrogen fluoride, 19.5 g (0.18 mol) of 2-toluidine, and 3.0 g (45 mmol) of boron trifluoride were weighed in a 100 mL stainless steel autoclave reactor equipped with a pressure gauge, a thermometer protection tube, an insertion tube, and a stirring motor, heated in an oil bath at 150° C., and reacted at an absolute pressure of 1.3 MPa for 5 hours. The reaction solution was poured into 300 g of ice, 210 g of a 48% potassium hydroxide aqueous solution was added thereto for neutralization, and an organic matter was extracted with 300 g of ethyl acetate. In a case where the extracted organic layer was analyzed by gas chromatography, the conversion rate of 2-toluidine was 98%. The organic layer recovered by the extraction operation was washed with 150 g of water and further washed with 150 g of saturated sodium bicarbonate water, and then the organic layer was recovered by the liquid separation operation. The organic layer was concentrated with an evaporator to obtain a target product 1,1,1-trifluoro-2,2-bis(3-methyl-4-aminophenyl)ethane of Formula [3] in a yield of 96% and an isomer ratio of 96/4. 25 g of the obtained crude crystals and 75 g of toluene were added to a 200 mL glass reactor equipped with a thermometer protection tube and a stirring motor, the temperature was raised to 90° C. to completely dissolve the crystals, and 50 g of heptane was added dropwise over 1 hour to precipitate crystals. After the temperature was lowered to 30° C., the crystals recovered by filtration were dried with an evaporator to obtain a target product 1,1,1-trifluoro-2,2-bis(3-methyl-4-aminophenyl)ethane (sometimes referred to as "BIS-3-AT-EF") in a yield of 87%, a purity of 99.8%, and an isomer ratio of equal to or more than 99% (2,2-bis(3-methyl-4-aminophenyl) form).

[Physical Properties Data]

1,1,1-trifluoro-2,2-bis(3-methyl-4-aminophenyl)ethane $^1$H-NMR (400 MHz, CDCl$_3$) δ (ppm): 2.13 (6H, s), 3.14 (4H, s), 4.41 (1H, q, J=10.4 Hz), 6.62 (2H, d, J=10.4 Hz), 7.01 (2H, s), 7.02 (2H, d, J=8.3 Hz)
$^{19}$F-NMR (400 MHz, CDCl$_3$, CFCl$_3$) δ (ppm): −66.7 (3F, d, J=11.5 Hz)

Synthesis Example 3 of Diamine (Synthesis of BIS-2-AT-EF)

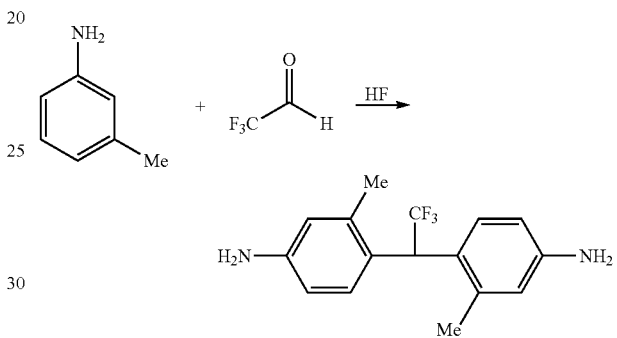

5.3 g (fluoral: 30 mmol, hydrogen fluoride: 0.12 mol) of the fluoral-containing mixture (hydrogen fluoride: 44% by weight, hydrogen chloride: 1% by weight, organic matter: 55% by weight) prepared with reference to Japanese Unexamined Patent Publication No. 2018-115146, 9.6 g (0.48 mol) of hydrogen fluoride, and 6.5 g (60 mmol) of 3-toluidine were weighed in a 100 mL stainless steel autoclave reactor equipped with a pressure gauge, a thermometer protection tube, an insertion tube, and a stirring motor, heated in an oil bath at 150° C., and reacted at an absolute pressure of 1.3 MPa for 5 hours. The reaction solution was poured into 100 g of ice, 70 g of a 48% potassium hydroxide aqueous solution was added thereto for neutralization, and an organic matter was extracted with 100 g of ethyl acetate. In a case where the extracted organic layer was analyzed by gas chromatography, the conversion rate of 3-toluidine was 83%. The organic layer recovered by the extraction operation was washed with 50 g of water and further washed with 50 g of saturated sodium bicarbonate water, and then the organic layer was recovered by the liquid separation operation. The organic layer was concentrated with an evaporator to obtain a target product 1,1,1-trifluoro-2,2-bis(2-methyl-4-aminophenyl)ethane (sometimes referred to as "BIS-2-AT-EF") in a yield of 71% and an isomer ratio of 97/2/1 (2,2-bis(2-methyl-4-aminophenyl) form/unidentified/unidentified).

[Physical Properties Data]

1,1,1-trifluoro-2,2-bis(2-methyl-4-aminophenyl)ethane $^1$H-NMR (400 MHz, CDCl$_3$) δ (ppm): 2.21 (6H, s), 3.58 (4H, bs), 4.83 (1H, q, J=9.6 Hz), 6.48 (2H, s), 6.50 (2H, d, J=9.4 Hz) 7.17 (2H, d, J=8.7 Hz)

$^{19}$F-NMR (400 MHz, CDCl$_3$, CFCl$_3$) δ (ppm): −65.6 (3F, d, J=11.6 Hz)

Synthesis Example 4 of Diamine (Synthesis of BIS-3, 5-AX-EF)

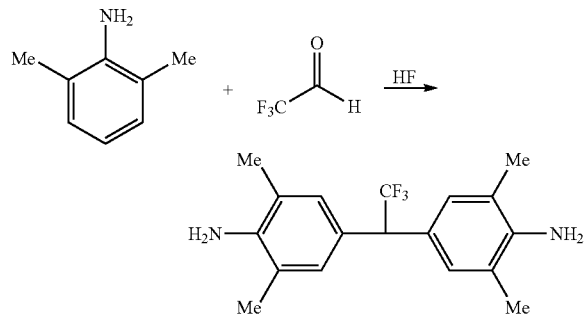

5.3 g (fluoral: 30 mmol, hydrogen fluoride: 0.12 mol) of the fluoral-containing mixture (hydrogen fluoride: 44% by weight, hydrogen chloride: 1% by weight, organic matter: 55% by weight) prepared with reference to Japanese Unexamined Patent Publication No. 2018-115146, 9.6 g (0.48 mol) of hydrogen fluoride, and 7.3 g (60 mmol) of 2,6-xylidine were weighed in a 100 mL stainless steel autoclave reactor equipped with a pressure gauge, a thermometer protection tube, an insertion tube, and a stirring motor, heated in an oil bath at 150° C., and reacted at an absolute pressure of 1.3 MPa for 5 hours. The reaction solution was poured into 100 g of ice, 70 g of a 48% potassium hydroxide aqueous solution was added thereto for neutralization, and an organic matter was extracted with 100 g of ethyl acetate. In a case where the extracted organic layer was analyzed by gas chromatography, the conversion rate of 2,6-xylidine was 99%. The organic layer recovered by the extraction operation was washed with 50 g of water and further washed with 50 g of saturated sodium bicarbonate water, and then the organic layer was recovered by the liquid separation operation. The organic layer was concentrated with an evaporator to obtain a target product 1,1,1-trifluoro-2,2-bis(3,5-dimethyl-4-aminophenyl)ethane of Formula [4] (sometimes referred to as "BIS-3,5-AX-EF") in a yield of 95% and an isomer ratio of 97/3 (2,2-bis(3,5-dimethyl-4-aminophenyl) form/unidentified).

[Physical Properties Data]

1,1,1-trifluoro-2,2-bis(3,5-dimethyl-4-aminophenyl)ethane $^1$H-NMR (400 MHz, CDCl$_3$) δ (ppm): 2.15 (12H, s), 3.55 (4H, s), 4.36 (1H, q, J=10.4 Hz), 6.62 (2H, d, J=10.4 Hz), 6.93 (4H, s)
$^{19}$F-NMR (400 MHz, CDCl$_3$, CFCl$_3$) δ (ppm): −66.6 (3F, d, J=8.6 Hz)

Synthesis Example 5 of Diamine (Synthesis of BIS-2,5-AX-EF)

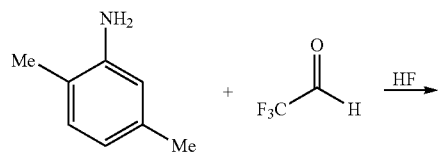

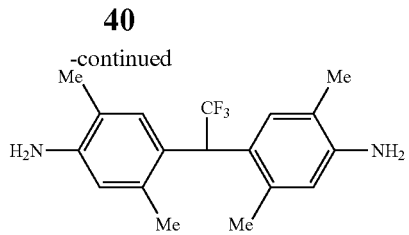

5.3 g (fluoral: 30 mmol, hydrogen fluoride: 0.12 mol) of the fluoral-containing mixture (hydrogen fluoride: 44% by weight, hydrogen chloride: 1% by weight, organic matter: 55% by weight) prepared with reference to Japanese Unexamined Patent Publication No. 2018-115146, 9.6 g (0.48 mol) of hydrogen fluoride, and 7.3 g (60 mmol) of 2,5-xylidine were weighed in a 100 mL stainless steel autoclave reactor equipped with a pressure gauge, a thermometer protection tube, an insertion tube, and a stirring motor, heated in an oil bath at 150° C., and reacted at an absolute pressure of 1.3 MPa for 5 hours. The reaction solution was poured into 100 g of ice, 70 g of a 48% potassium hydroxide aqueous solution was added thereto for neutralization, and an organic matter was extracted with 100 g of ethyl acetate. In a case where the extracted organic layer was analyzed by gas chromatography, the conversion rate of 2,5-xylidine was 98%. The organic layer recovered by the extraction operation was washed with 50 g of water and further washed with 50 g of saturated sodium bicarbonate water, and then the organic layer was recovered by the liquid separation operation. The organic layer was concentrated with an evaporator to obtain a target product 1,1,1-trifluoro-2,2-bis(2,5-dimethyl-4-aminophenyl)ethane (sometimes referred to as "BIS-2,5-AX-EF") in a yield of 94% and an isomer ratio of 99/1 (2,2-bis(2,5-dimethyl-4-aminophenyl) form/unidentified).

[Physical Properties Data]

1,1,1-trifluoro-2,2-bis(2,5-dimethyl-4-aminophenyl)ethane $^1$H-NMR (400 MHz, CDCl$_3$) δ (ppm): 2.12 (6H, s), 2.19 (6H, s), 3.53 (4H, bs), 4.80 (1H, q, J=9.6 Hz), 6.45 (2H, s, 7.04 (2H, s)
$^{19}$F-NMR (400 MHz, CDCl$_3$, CFCl$_3$) δ (ppm): −65.5 (3F, d, J=8.7 Hz)

Synthesis Example 6 of Diamine (Synthesis of BIS-2,3-AX-EF)

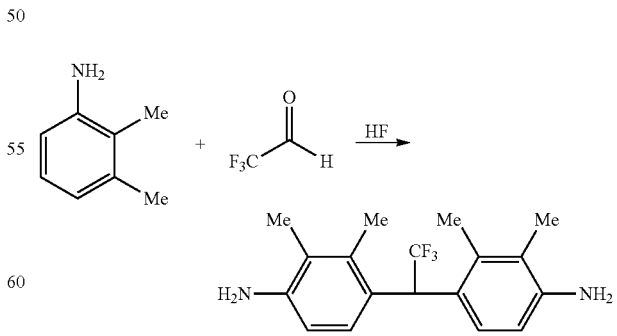

15.5 g (fluoral: 82 mmol, hydrogen fluoride: 0.37 mol) of the fluoral-containing mixture (hydrogen fluoride: 48% by weight, hydrogen chloride: less than 0.1% by weight, organic matter: 52% by weight) prepared with reference to Japanese Unexamined Patent Publication No. 2018-115146, 12.4 g (0.62 mol) of hydrogen fluoride, and 20 g (165 mmol) of 2,3-xylidine were weighed in a 100 mL stainless steel autoclave reactor equipped with a pressure gauge, a thermometer protection tube, an insertion tube, and a stirring motor, heated in an oil bath at 150° C., and reacted at an absolute pressure of 0.55 MPa for 18 hours. The reaction solution was poured into 100 g of ice, 116 g of a 48% potassium hydroxide aqueous solution was added thereto for neutralization, and an organic matter was extracted with 100 g of ethyl acetate. In a case where the extracted organic layer was analyzed by gas chromatography, the conversion rate of 2,3-xylidine was 90%. The organic layer recovered by the extraction operation was washed with 50 g of water and further washed with 50 g of saturated sodium bicarbonate water, and then the organic layer was recovered by the liquid separation operation. The organic layer was concentrated with an evaporator to obtain a target product 1,1,1-trifluoro-2,2-bis(2,3-dimethyl-4-aminophenyl)ethane (sometimes referred to as "BIS-2,3-AX-EF") in a yield of 77% and an isomer ratio of 99/1 (2,2-bis(2,3-dimethyl-4-aminophenyl) form/unidentified).

[Physical Properties Data]

1,1,1-trifluoro-2,2-bis(2,3-dimethyl-4-aminophenyl) ethane $^1$H-NMR (400 MHz, CDCl$_3$) δ (ppm): 2.10 (6H, s), 2.18 (6H, s), 4.19 (4H, bs), 5.01 (1H, q, J=9.6 Hz), 6.59 (2H, d, J=8.4 Hz), 7.07 (2H, d, J=8.4 Hz)
$^{19}$F-NMR (400 MHz, CDCl$_3$, CFCl$_3$) δ (ppm): −64.6 (3F, d, J=9.2 Hz)

[Synthesis Example 7 of Diamine (Synthesis of BIS-A-A)]L 1

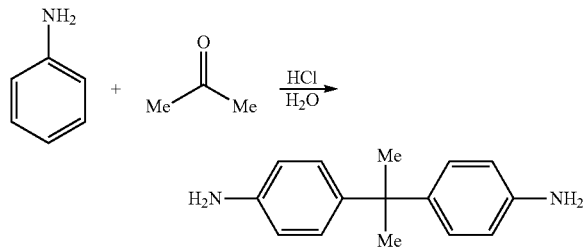

With reference to Japanese Unexamined Patent Publication No. 2012-140345, 500.3 g (3.86 mol) of aniline hydrochloride, 199.1 g of water, and 80.0 g (1.38 mol) of acetone were weighed in a 1 L stainless steel autoclave reactor equipped with a pressure gauge, a thermometer protection tube, an insertion tube, and a stirring motor, heated in an oil bath at 190° C., and reacted at an absolute pressure of 1.3 MPa for 5 hours. The reaction solution was poured into 206 g of water, 322 g (3.86 mol) of a 48% sodium hydroxide aqueous solution was added thereto for neutralization, and an organic layer was extracted with 2 kg of ethyl acetate. The organic layer recovered by the extraction operation was washed with 1 kg of water, and then the organic layer was recovered by a liquid separation operation. The organic layer was concentrated with an evaporator to obtain a crude reaction product. The obtained crude reaction product was charged into a 1 L glass distillation device equipped with a stirrer, a thermometer protection tube, and a reduced-pressure distillation device. The pressure was reduced to an absolute pressure of 50 kPa, followed by heating in an oil bath at 90° C. for 1 hour to distill off low boiling point components including ethyl acetate. Further, the pressure was reduced to an absolute pressure of 0.1 kPa while raising the temperature to 170° C. over 3 hours, whereby a component having a boiling point lower than that of 2,2-bis(4-aminophenyl)propane was distilled off. Then, the temperature was lowered to 90° C., 200 g of toluene and 100 g of heptane were added, and the mixture was cooled to room temperature over 2 hours to precipitate a solid. 126.9 g of a brown solid was recovered by suction filtration. The brown solid was mixed with 300 g of toluene and heated and dissolved in an oil bath at 100° C., followed by cooling to room temperature over 3 hours to precipitate a white solid. The solid recovered by suction filtration was dried with an evaporator to obtain a target product 2,2-bis(4-aminophenyl) propane (sometimes referred to as "BIS-A-A") in a yield of 19% and a purity of 99%.

Example 1

13.3 g (50 mmol) of 1,1,1-trifluoro-2,2-bis (4-aminophenyl)ethane (sometimes referred to as BIS-A-EF) prepared in Synthesis Example 1 shown in the following formula and 22.2 g (50 mmol) of 4,4'-hexafluoroisopropylidenediphthalic anhydride (hereinafter, sometimes referred to as 6FDA) were added to a 500 mL three-necked flask equipped with a nitrogen inlet tube and a stirring blade, and 142.1 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. As a result of GPC measurement of the solution, Mw=471820 and Mw/Mn=2.7. The solution of polyamide acid was applied onto a glass substrate using a spin coater, followed by continuous heating at 130° C. for 30 minutes, 200° C. for 1 hour, and 300° C. for 1 hour while gradually raising the temperature to obtain a film on the glass substrate. The film thickness was 21 μm. From the measurement results of IR spectrum, it was confirmed that 1718 cm$^{-1}$ and 1786 cm$^{-1}$ had absorption peculiar to an imide group, and the film was made of polyimide.

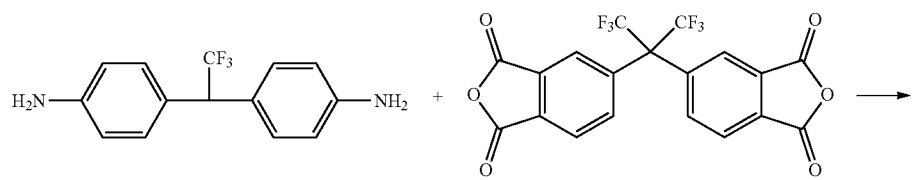

-continued

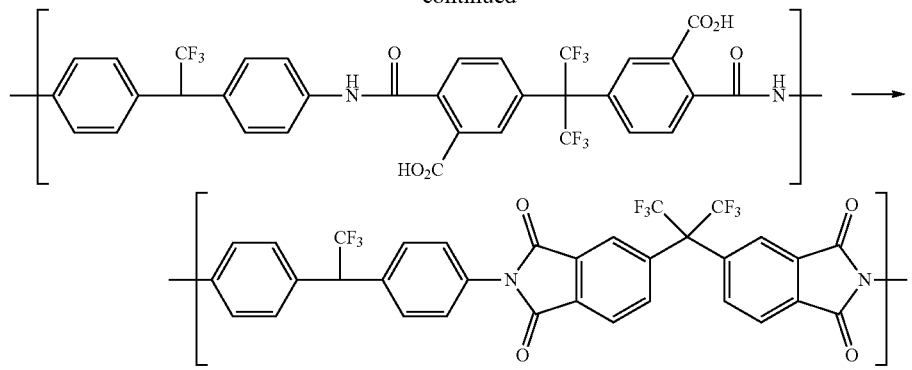

Example 2

20.6 g (70 mmol) of 1,1,1-trifluoro-2,2-bis(3-methyl-4-aminophenyl)ethane (sometimes referred to as BIS-3-AT-EF) prepared in Synthesis Example 2 shown in the following formula and 31.2 g (70 mmol) of 6FDA were added to a 500 mL three-necked flask equipped with a nitrogen inlet tube and a stirring blade, and 206.8 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. As a result of GPC measurement of the solution, Mw=243857 and Mw/Mn=2.2. The solution of polyamide acid was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 23 μm. From the measurement results of IR spectrum, it was confirmed that 1720 cm$^{-1}$ and 1786 cm$^{-1}$ had absorption peculiar to an imide group, and the optical film was made of polyimide.

Example 3

17.7 g (70 mmol) of 1,1,1-trifluoro-2,2-bis(2-methyl-4-aminophenyl)ethane (sometimes referred to as BIS-2-AT-EF) prepared in Synthesis Example 3 shown in the following formula and 26.6 g (60 mmol) of 6FDA were added to a 500 mL three-necked flask equipped with a nitrogen inlet tube and a stirring blade, and 103 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. As a result of GPC measurement of the solution, Mw=289916 and Mw/Mn=2.7. The solution of polyamide acid was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 23 μm. From the measurement results of IR spectrum, it was confirmed that 1720 cm$^{-1}$ and 1785 cm$^{-1}$ had absorption peculiar to an imide group, and the optical film was made of polyimide.

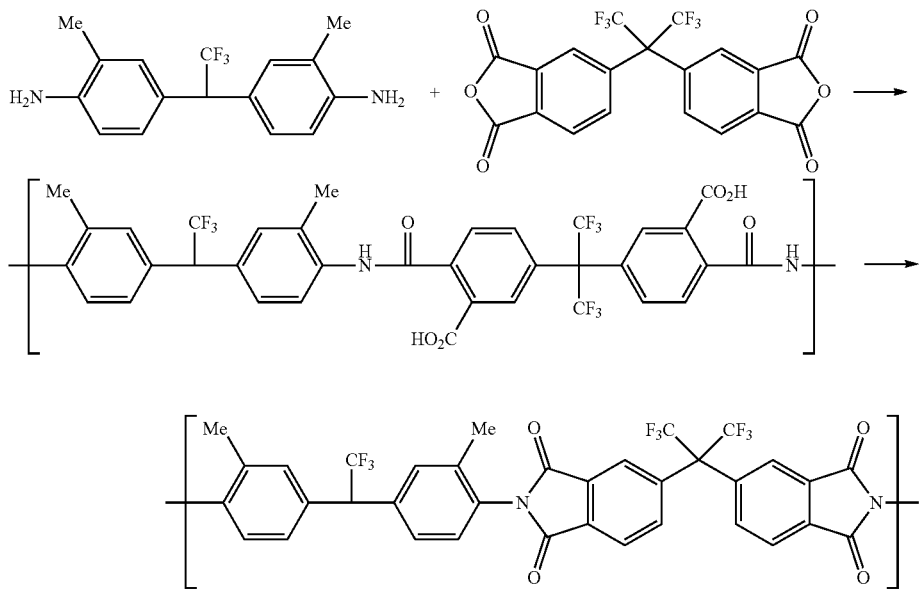

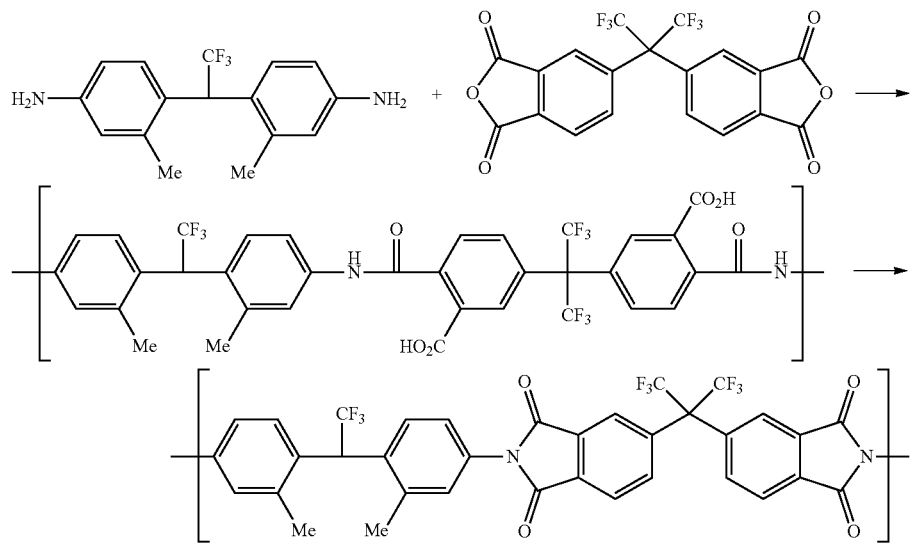

Example 4

24.2 g (75 mmol) of 1,1,1-trifluoro-2,2-bis (3,5-dimethyl-4-aminophenyl) ethane (sometimes referred to as BIS-3,5-AX-EF) prepared in Synthesis Example 4 shown in the following formula and 33.3 g (75 mmol) of 6FDA were added to a 500 mL three-necked flask equipped with a nitrogen inlet tube and a stirring blade, and 134.1 g of DMAc was further added as an organic solvent. This was followed by stirring at room temperature (20° C.) for 23 hours under a nitrogen atmosphere to obtain a solution of polyamide acid. 12.5 g (158 mmol) of pyridine and 16.1 g (158 mmol) of acetic anhydride were added in this order to the obtained reaction solution which was then stirred at room temperature (20° C.) for 2 hours under a nitrogen atmosphere to carry out imidization. This was followed by filtration under pressure to prepare a solution of polyimide. As a result of GPC measurement of the solution, Mw=149137 and Mw/Mn=2.3. The solution of polyimide was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 25 μm. From the measurement results of IR spectrum, it was confirmed that 1723 cm$^{-1}$ and 1787 cm$^{-1}$ had absorption peculiar to an imide group, and the optical film was made of polyimide.

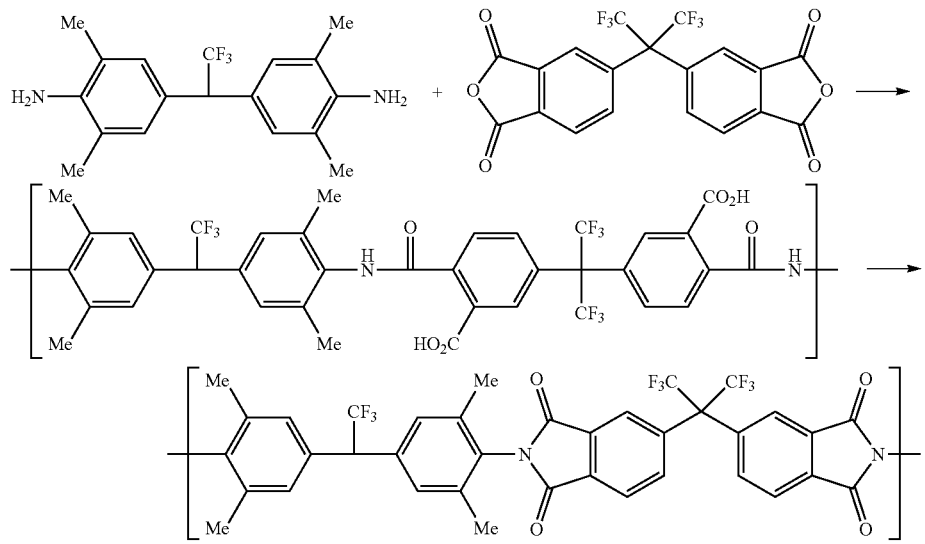

Example 5

22.6 g (70 mmol) of 1,1,1-trifluoro-2,2-bis(2,5-dimethyl-4-aminophenyl)ethane (sometimes referred to as BIS-2,5-AX-EF) prepared in Synthesis Example 5 shown in the following formula and 31.2 g (70 mmol) of 6FDA were added to a 500 mL three-necked flask equipped with a nitrogen inlet tube and a stirring blade, and 125 g of DMAc was further added as an organic solvent. This was followed by stirring at room temperature (20° C.) for 24 hours under a nitrogen atmosphere to obtain a solution of polyamide acid. 11.6 g (147 mmol) of pyridine and 15.0 g (147 mmol) of acetic anhydride were added in this order to the obtained reaction solution which was then stirred at room temperature (20° C.) for 3 hours under a nitrogen atmosphere to carry out imidization. Thereafter, DMAc was added to dilute the imidized reaction solution which was then filtered under pressure to prepare a solution of polyimide. As a result of GPC measurement of the solution, Mw=337504 and Mw/Mn=2.3. The solution of polyimide was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 22 μm. From the measurement results of IR spectrum, it was confirmed that 1721 cm$^{-1}$ and 1786 cm$^{-1}$ had absorption peculiar to an imide group, and the optical film was made of polyimide.

added to a 500 mL three-necked flask equipped with a nitrogen inlet tube and a stirring blade, and 161 g of DMAc was further added as an organic solvent. This was followed by stirring at room temperature (20° C.) for 24 hours under a nitrogen atmosphere to obtain a solution of polyamide acid. 11.6 g (147 mmol) of pyridine and 15.0 g (147 mmol) of acetic anhydride were added in this order to the obtained reaction solution which was then stirred at room temperature (20° C.) for 3 hours under a nitrogen atmosphere to carry out imidization. Thereafter, DMAc was added to dilute the imidized reaction solution which was then filtered under pressure to prepare a solution of polyimide. As a result of GPC measurement of the solution, Mw=192832 and Mw/Mn=2.4. The solution of polyimide was applied onto a glass substrate using a spin coater, followed by continuous heating at 130° C. for 30 minutes, 200° C. for 1 hour, and 300° C. for 1 hour while gradually raising the temperature

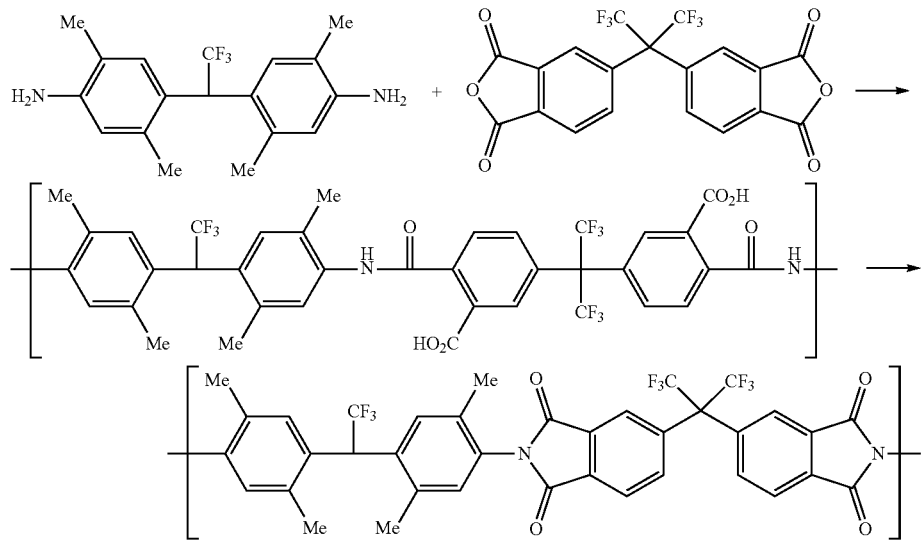

Example 6

22.6 g (70 mmol) of 1,1,1-trifluoro-2,2-bis(2,3-dimethyl-4-aminophenyl)ethane (sometimes referred to as BIS-2,3-AX-EF) prepared in Synthesis Example 6 shown in the following formula and 31.1 g (70 mmol) of 6FDA were to obtain an optical film on the glass substrate. The film thickness was 30 μm. From the measurement results of IR spectrum, it was confirmed that 1723 cm$^{-1}$ and 1787 cm$^{-1}$ had absorption peculiar to an imide group, and the optical film was made of polyimide.

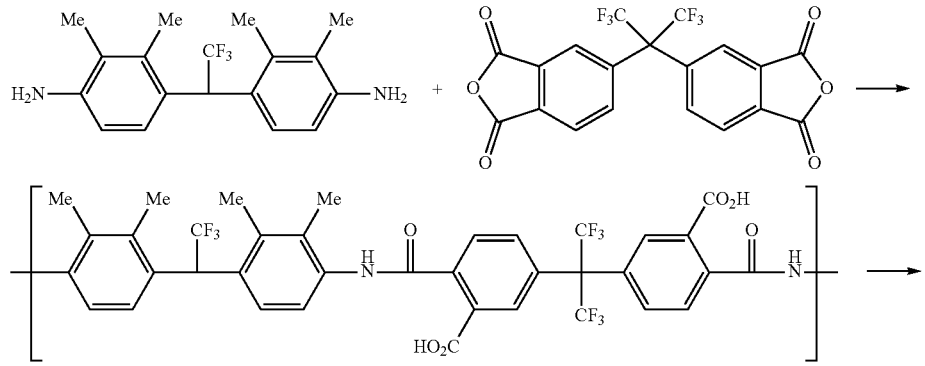

-continued

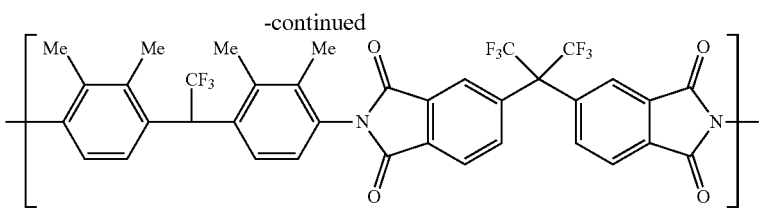

Example 7

20.6 g (70 mmol) of 1,1,1-trifluoro-2,2-bis(3-methyl-4-aminophenyl)ethane (sometimes referred to as BIS-3-AT-EF) prepared in Synthesis Example 2 shown in the following formula and 21.7 g (70 mmol) of 4,4'-oxydiphthalic anhydride (hereinafter, sometimes referred to as ODPA) were added to a 500 mL three-necked flask equipped with a nitrogen inlet tube and a stirring blade, and 169.2 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. As a result of GPC measurement of the solution, Mw=199383 and Mw/Mn=4.0. The solution of polyamide acid was applied onto a glass substrate using a spin coater, followed by continuous heating at 130° C. for 30 minutes, 200° C. for 1 hour, and 250° C. for 2 hours while gradually raising the temperature to obtain an optical film on the glass substrate. The film thickness was 24 μm. From the measurement results of IR spectrum, it was confirmed that 1714 cm$^{-1}$ and 1778 cm$^{-1}$ had absorption peculiar to an imide group, and the optical film was made of polyimide.

Example 8

16.2 g (50 mmol) of 1,1,1-trifluoro-2,2-bis(3,5-dimethyl-4-aminophenyl)ethane (sometimes referred to as BIS-3,5-AX-EF) prepared in Synthesis Example 4 shown in the following formula and 15.6 g (50 mmol) of 4,4'-oxydiphthalic anhydride (ODPA) were added to a 500 mL three-necked flask equipped with a nitrogen inlet tube and a stirring blade, and 73.8 g of DMAc was further added as an organic solvent. This was followed by stirring at 40° C. for 1 hour under a nitrogen atmosphere and further stirring at room temperature (20° C.) for 23 hours to obtain a reaction solution. Thereafter, DMAc was added to dilute the reaction solution which was then filtered under pressure to prepare a solution of polyamide acid. 8.3 g (105 mmol) of pyridine and 10.7 g (105 mmol) of acetic anhydride were added in this order to the obtained reaction solution which was then stirred at room temperature (20° C.) for 3 hours under a nitrogen atmosphere to carry out imidization. Thereafter, DMAc was added to dilute the imidized reaction solution which was then filtered under pressure to prepare a solution of polyimide. As a result of GPC measurement of the solution, Mw=100473 and Mw/Mn=3.3. An optical film was obtained on a glass substrate by continuously heating at 130° C. for 30 minutes, 200° C. for 1 hour, and 300° C. for 1 hour while gradually raising the temperature. The film thickness was 27 μm. From the measurement results of IR spectrum, it was confirmed that 1717 cm$^{-1}$ and 1777 cm$^{-1}$ had absorption peculiar to an imide group, and the optical film was made of polyimide.

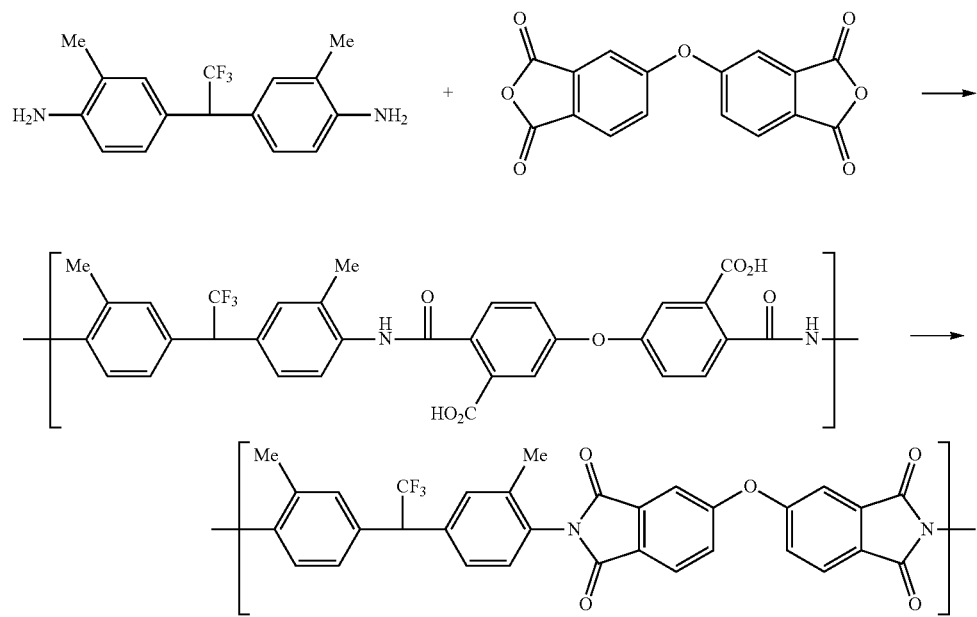

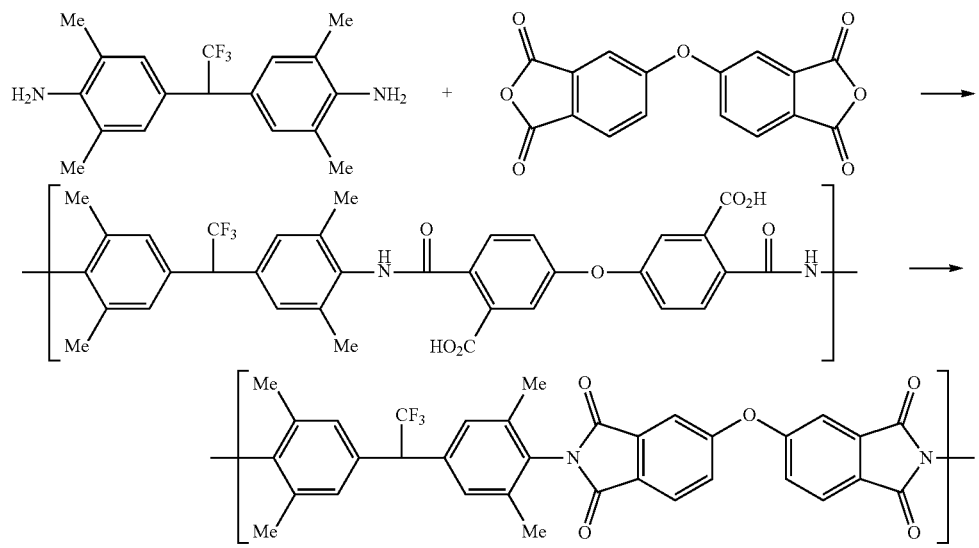

Example 9

29.4 g (100 mmol) of 1,1,1-trifluoro-2,2-bis(3-methyl-4-aminophenyl)ethane (sometimes referred to as BIS-3-AT-EF) prepared in Synthesis Example 2 shown in the following formula and 29.4 g (100 mmol) of 4,4'-biphthalic anhydride (hereinafter, sometimes referred to as BPDA) were added to a 500 mL three-necked flask equipped with a nitrogen inlet tube and a stirring blade, and 197.0 g of DMAc was further added as an organic solvent. This was followed by stirring at room temperature (20° C.) for 24 hours under a nitrogen atmosphere to obtain a solution of polyamide acid. 16.6 g (210 mmol) of pyridine and 21.4 g (210 mmol) of acetic anhydride were added in this order to the obtained reaction solution which was then stirred at room temperature (20° C.) for 3 hours under a nitrogen atmosphere to carry out imidization. Thereafter, DMAc was added to dilute the imidized reaction solution which was then filtered under pressure to prepare a solution of polyimide. As a result of GPC measurement of the solution, Mw=215115 and Mw/Mn=3.4. The solution of polyimide was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 24 μm. From the measurement results of IR spectrum, it was confirmed that 1711 cm$^{-1}$ and 1776 cm$^{-1}$ had absorption peculiar to an imide group, and the optical film was made of polyimide.

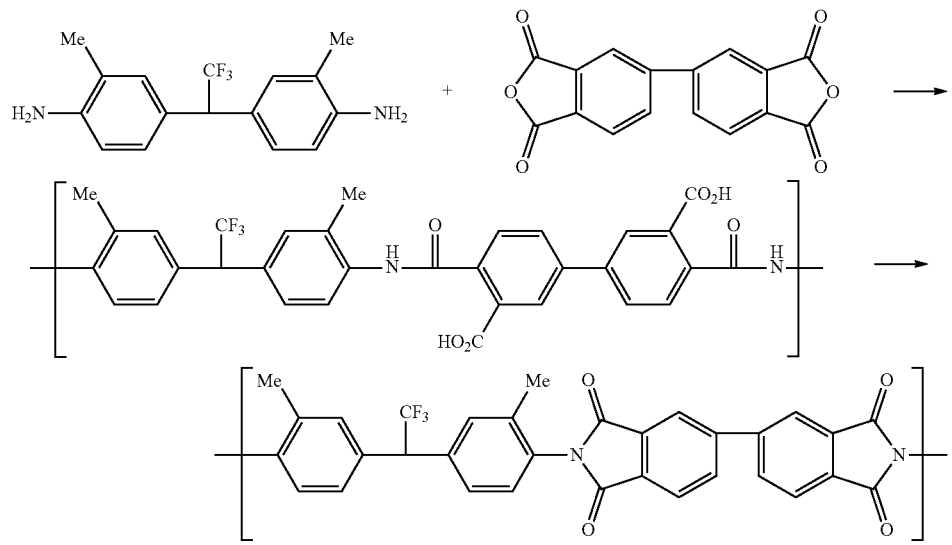

Example 10

16.2 g (50 mmol) of 1,1,1-trifluoro-2,2-bis(3,5-dimethyl-4-aminophenyl)ethane (sometimes referred to as BIS-3,5-AX-EF) prepared in Synthesis Example 4 shown in the following formula and 14.7 g (50 mmol) of 4,4'-biphthalic anhydride (BPDA) were added to a 500 mL three-necked flask equipped with a nitrogen inlet tube and a stirring blade, and 71.9 g of DMAc was further added as an organic solvent. This was followed by stirring at 40° C. for 1 hour under a nitrogen atmosphere and further stirring at room temperature (20° C.) for 23 hours to obtain a solution of polyamide acid. 8.3 g (105 mmol) of pyridine and 10.7 g (105 mmol) of acetic anhydride were added in this order to the obtained reaction solution which was then stirred at room temperature (20° C.) for 3 hours under a nitrogen atmosphere to carry out imidization. Thereafter, DMAc was added to dilute the imidized reaction solution which was then filtered under pressure to prepare a solution of polyimide. As a result of GPC measurement of the solution, Mw=121272 and Mw/Mn=3.3. The solution of polyimide was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 26 μm. From the measurement results of IR spectrum, it was confirmed that 1713 cm$^{-1}$ and 1776 cm$^{-1}$ had absorption peculiar to an imide group, and the optical film was made of polyimide.

formula and 23.0 g (71 mmol) of 3,3',4,4'-benzophenone tetracarboxylic dianhydride (hereinafter, sometimes referred to as BTDA) were added to a 500 mL three-necked flask equipped with a nitrogen inlet tube and a stirring blade, and 133 g of DMAc was further added as an organic solvent. This was followed by stirring at room temperature (20° C.) for 24 hours under a nitrogen atmosphere to obtain a solution of polyamide acid. 11.9 g (150 mmol) of pyridine and 15.0 g (150 mmol) of acetic anhydride were added in this order to the obtained reaction solution which was then stirred at room temperature (20° C.) for 3 hours under a nitrogen atmosphere to carry out imidization. Thereafter, DMAc was added to dilute the imidized reaction solution which was then filtered under pressure to prepare a solution of polyimide. As a result of GPC measurement of the solution, Mw=70,000 and Mw/Mn=2.6. The solution of polyimide was applied onto a glass substrate using a spin coater, followed by continuous heating at 130° C. for 30 minutes, 200° C. for 1 hour, and 300° C. for 1 hour while gradually

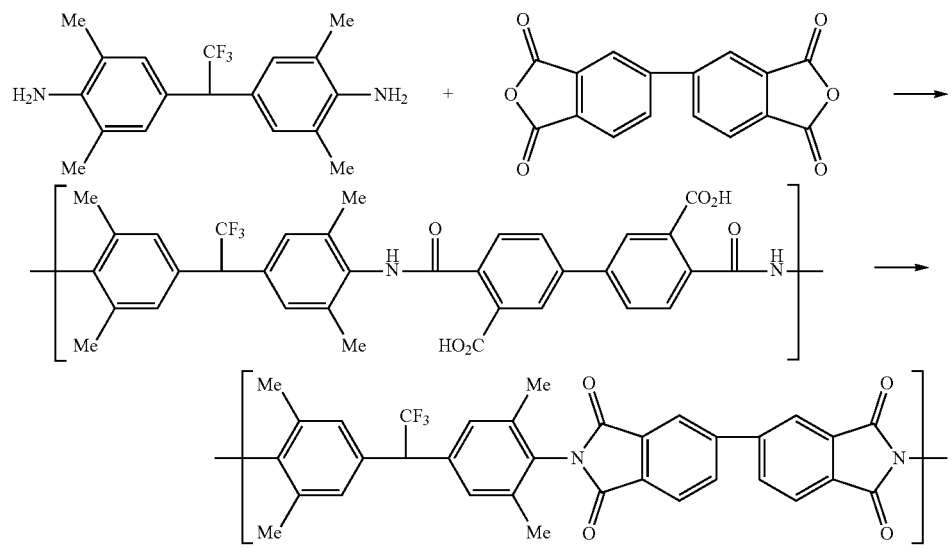

Example 11

21.0 g (71 mmol) of 1,1,1-trifluoro-2,2-bis(3-methyl-4-aminophenyl)ethane (sometimes referred to as BIS-3-AT-EF) prepared in Synthesis Example 2 shown in the following raising the temperature to obtain an optical film on the glass substrate. The film thickness was 26 μm. From the measurement results of IR spectrum, it was confirmed that 1719 cm$^{-1}$ and 1780 cm$^{-1}$ had absorption peculiar to an imide group, and the optical film was made of polyimide.

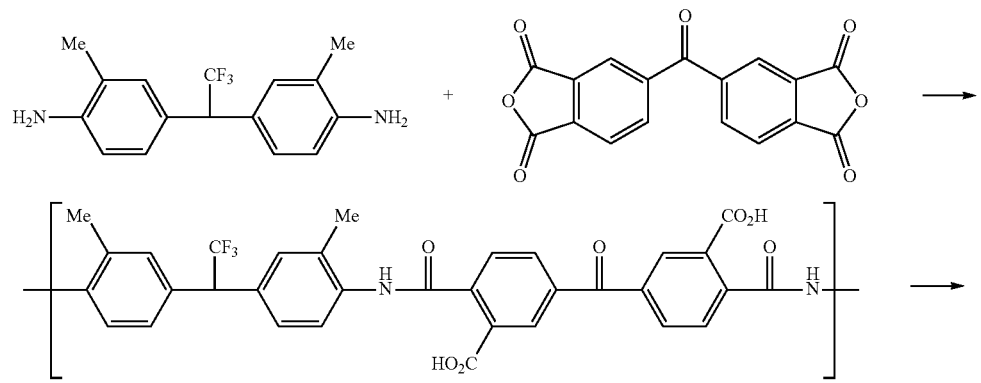

-continued

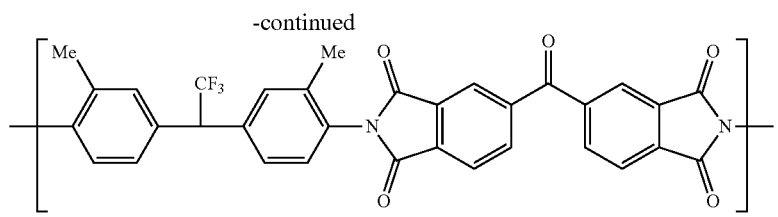

Example 12

21.0 g (65 mmol) of 1,1,1-trifluoro-2,2-bis(2,5-dimethyl-4-aminophenyl)ethane (sometimes referred to as BIS-2,5-AX-EF) prepared in Synthesis Example 5 shown in the following formula and 21.0 g (65 mmol) of BTDA were added to a 500 mL three-necked flask equipped with a nitrogen inlet tube and a stirring blade, and 100 g of DMAc was further added as an organic solvent. This was followed by stirring at room temperature (20° C.) for 24 hours under a nitrogen atmosphere to obtain a solution of polyamide acid. 10.8 g (137 mmol) of pyridine and 14.0 g (137 mmol) of acetic anhydride were added in this order to the obtained reaction solution which was then stirred at room temperature (20° C.) for 3 hours under a nitrogen atmosphere to carry out imidization. Thereafter, DMAc was added to dilute the imidized reaction solution which was then filtered under pressure to prepare a solution of polyimide. As a result of GPC measurement of the solution, Mw=68,000 and Mw/Mn=2.5. The solution of polyimide was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 30 μm. From the measurement results of IR spectrum, it was confirmed that 1721 cm$^{-1}$ and 1786 cm$^{-1}$ had absorption peculiar to an imide group, and the optical film was made of polyimide.

Comparative Example 1

14.9 g (75 mmol) of 4,4-methylenebisbenzenediamine (hereinafter, referred to as MDA) shown in the following formula and 33.3 g (75 mmol) of 6FDA were added to a 500 mL three-necked flask equipped with a nitrogen inlet tube and a stirring blade, and 273 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. As a result of GPC measurement of the solution, Mw=199171 and Mw/Mn=2.1. The solution of polyamide acid was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 25 μm. From the measurement results of IR spectrum, it was confirmed that 1718 cm$^{-1}$ and 1784 cm$^{-1}$ had absorption peculiar to an imide group, and the optical film was made of polyimide.

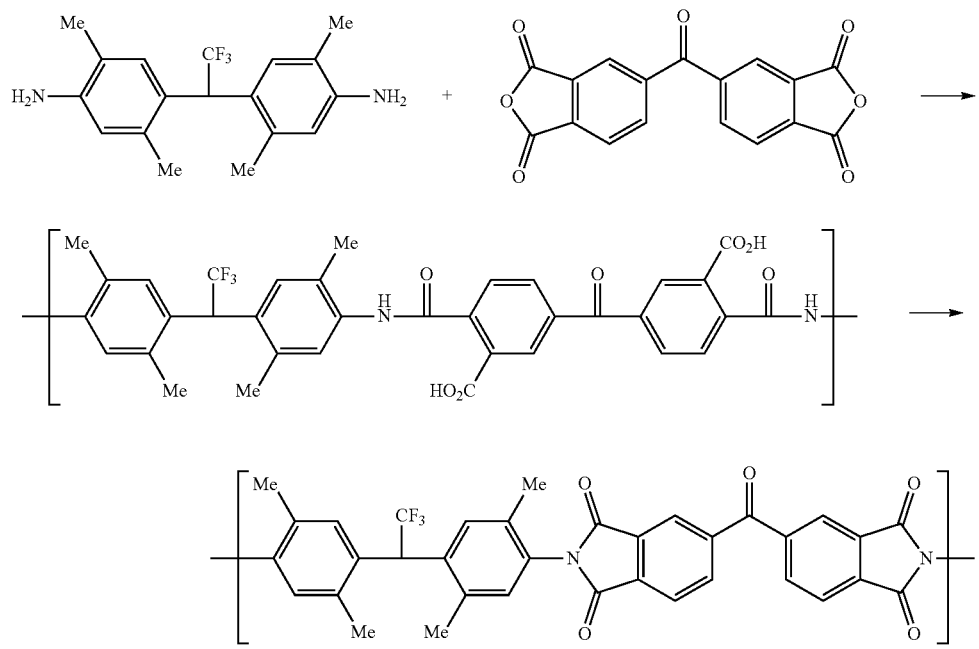

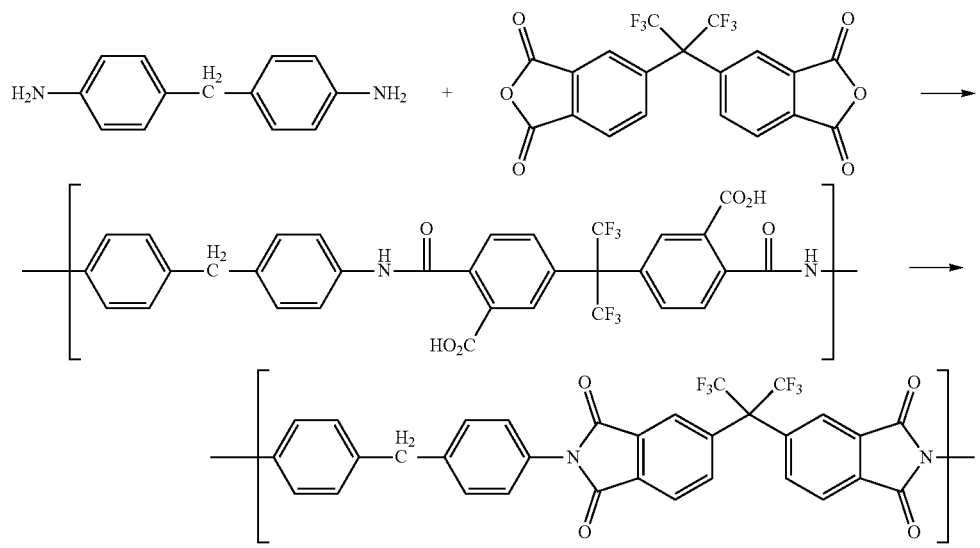

Comparative Example 2

15.8 g (70 mmol) of 2,2-bis(4-aminophenyl)propane (BIS-A-A) prepared in Synthesis Example 7 shown in the following formula and 31.1 g (70 mmol) of 6FDA were added to a 500 mL three-necked flask equipped with a nitrogen inlet tube and a stirring blade, and 213 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. As a result of GPC measurement of the solution, Mw=176064 and Mw/Mn=2.1. The solution of polyamide acid was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 28 µm. From the measurement results of IR spectrum, it was confirmed that 1717 cm$^{-1}$ and 1784 cm$^{-1}$ had absorption peculiar to an imide group, and the optical film was made of polyimide.

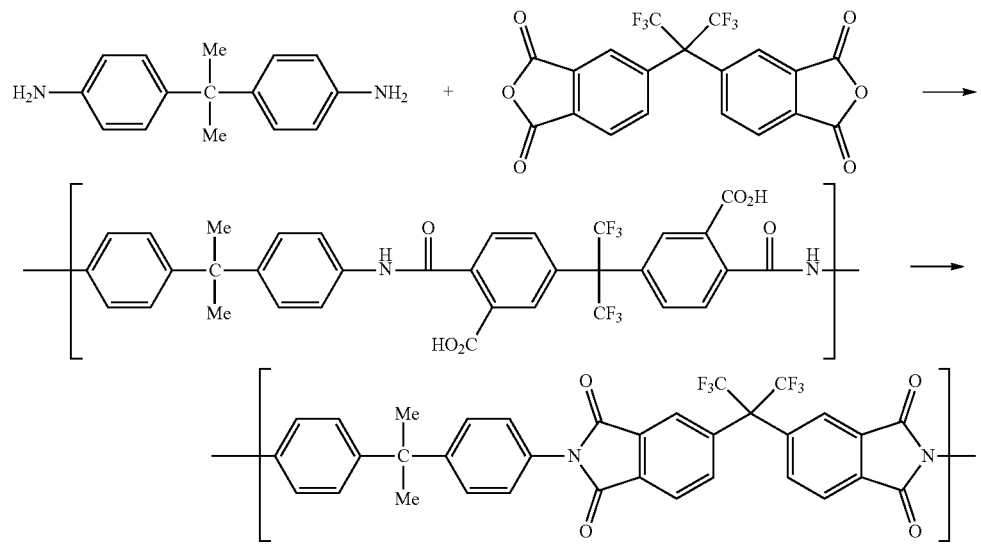

Comparative Example 3

12.5 g (37 mmol) of 2,2-bis(4-aminophenyl)hexafluoropropane (BIS-A-AF) prepared in Synthesis Example 7 shown in the following formula and 16.6 g (37 mmol) of 6FDA were added to a 500 mL three-necked flask equipped with a nitrogen inlet tube and a stirring blade, and 102 g of DMAc was further added as an organic solvent. This was followed by stirring at room temperature (20° C.) for 24 hours under a nitrogen atmosphere to obtain a reaction solution. This was followed by filtration under pressure to prepare a solution of polyamide acid. As a result of GPC measurement of the solution, Mw=259362 and Mw/Mn=2.7. The solution of polyamide acid was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 26 μm. From the measurement results of IR spectrum, it was confirmed that 1720 cm$^{-1}$ and 1787 cm$^{-1}$ had absorption peculiar to an imide group, and the optical film was made of polyimide.

temperature (20° C.) for 24 hours under a nitrogen atmosphere to obtain a reaction solution. This was followed by filtration under pressure to prepare a solution of polyamide acid. As a result of GPC measurement of the solution, Mw=147837 and Mw/Mn=2.7. The solution of polyamide acid was applied onto a glass substrate using a spin coater, followed by continuous heating at 130° C. for 30 minutes,

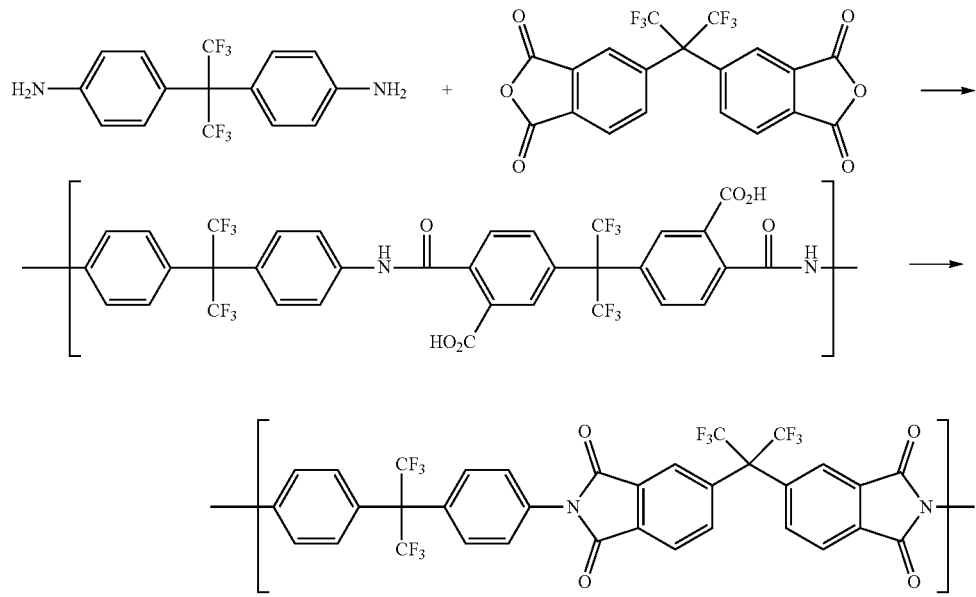

Comparative Example 4

10.0 g (31 mmol) of 2,2'-bistrifluoromethylbenzidine (hereinafter, referred to as TFMB) shown in the following formula and 13.8 g (31 mmol) of 6FDA were added to a 500 mL three-necked flask equipped with a nitrogen inlet tube and a stirring blade, and 159 g of DMAc was further added as an organic solvent. This was followed by stirring at room 200° C. for 1 hour, and 300° C. for 1 hour while gradually raising the temperature to obtain an optical film on the glass substrate. The film thickness was 27 μm. From the measurement results of IR spectrum, it was confirmed that 1724 cm$^{-1}$ and 1786 cm$^{-1}$ had absorption peculiar to an imide group, and the optical film was made of polyimide.

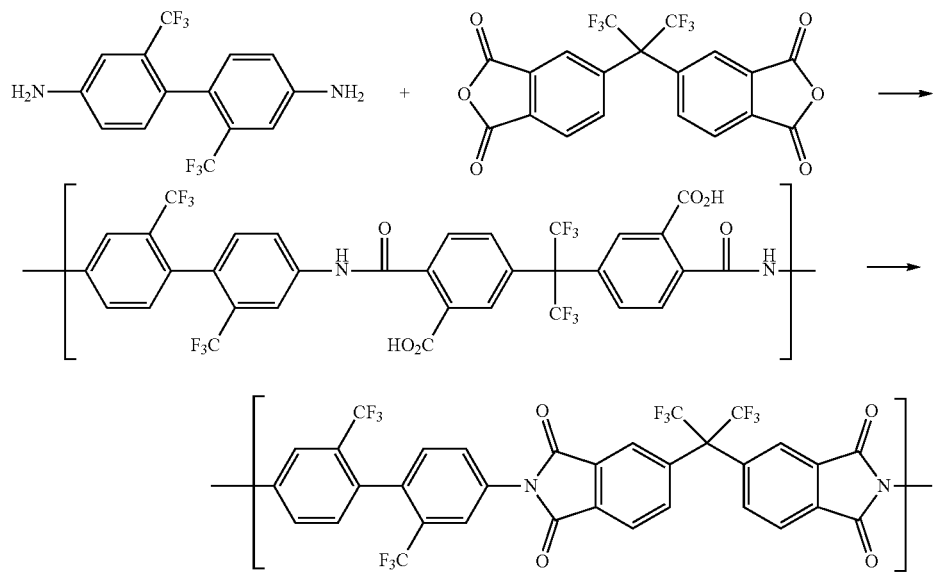

Comparative Example 51

14.9 g (75 mmol) of MDA shown in the following formula and 23.3 g (75 mmol) of ODPA were added to a 500 mL three-necked flask equipped with a nitrogen inlet tube and a stirring blade, and 150 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. As a result of GPC measurement of the solution, Mw=181515 and Mw/Mn=4.1. The solution of polyamide acid was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 25 μm. From the measurement results of IR spectrum, it was confirmed that 1710 cm$^{-1}$ and 1775 cm$^{-1}$ had absorption peculiar to an imide group, and the optical film was made of polyimide.

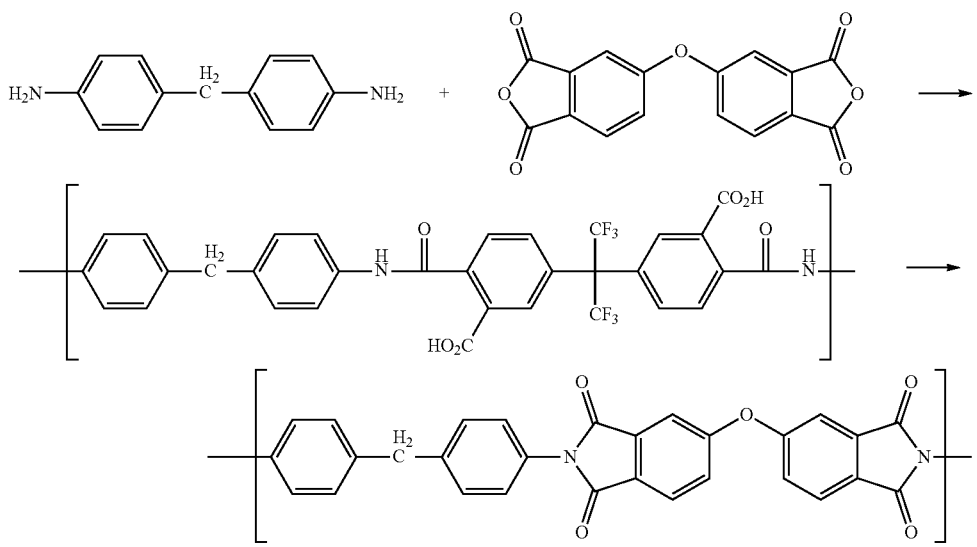

Comparative Example 6

15.8 g (70 mmol) of 2,2-bis(4-aminophenyl)propane (BIS-A-A) prepared in Synthesis Example 7 shown in the following formula and 21.7 g (70 mmol) of ODPA were added to a 500 mL three-necked flask equipped with a nitrogen inlet tube and a stirring blade, and 113 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. As a result of GPC measurement of the solution, Mw=93037 and Mw/Mn=3.6. The solution of polyamide acid was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 30 μm. From the measurement results of IR spectrum, it was confirmed that 1710 cm$^{-1}$ and 1776 cm$^{-1}$ had absorption peculiar to an imide group, and the optical film was made of polyimide.

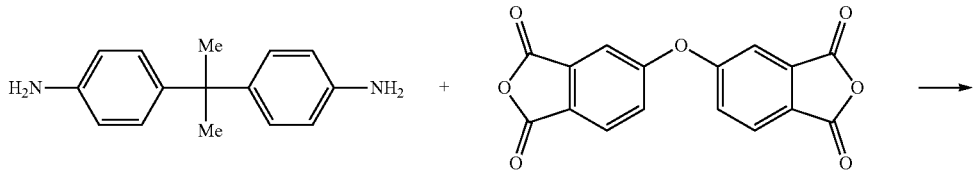

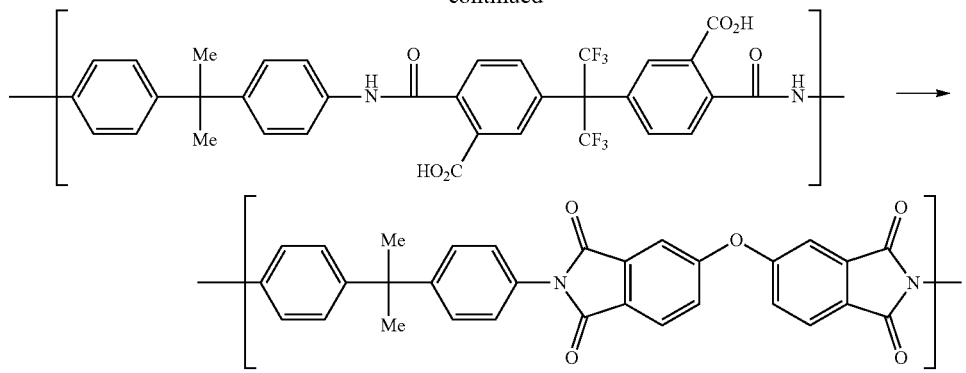

Comparative Example 7

12.5 g (37 mmol) of 2,2-bis(4-aminophenyl)hexafluoropropane (BIS-A-AF) and 11.6 g (37 mmol) of ODPA were added to a 500 mL three-necked flask equipped with a nitrogen inlet tube and a stirring blade, and 56 g of DMAc was further added as an organic solvent. This was followed by stirring at room temperature (20° C.) for 24 hours under a nitrogen atmosphere to obtain a reaction solution. This was followed by filtration under pressure to prepare a solution of polyamide acid. As a result of GPC measurement of the solution, Mw=294500 and Mw/Mn=6.0. The solution of polyamide acid was applied onto a glass substrate using a spin coater, followed by continuous heating at 130° C. for 30 minutes, 200° C. for 1 hour, and 300° C. for 1 hour while gradually raising the temperature to obtain a film on the glass substrate. The film thickness was 26 μm. From the measurement results of IR spectrum, it was confirmed that 1718 cm$^{-1}$ and 1780 cm$^{-1}$ had absorption peculiar to an imide group, and the film was made of polyimide.

Comparative Example 8

11.9 g (60 mmol) of MDA shown in the following formula and 17.7 g (60 mmol) of BPDA were added to a 500 mL three-necked flask equipped with a nitrogen inlet tube and a stirring blade, and 118 g of DMAc was further added as an organic solvent. This was followed by stirring at 50° C. for 30 minutes under a nitrogen atmosphere and further stirring at room temperature (20° C.) for 23 hours to obtain a reaction solution. Thereafter, DMAc was added to dilute the reaction solution which was then filtered under pressure to prepare a solution of polyamide acid. As a result of GPC measurement of the solution, Mw=59026 and Mw/Mn=11.0. The solution of polyamide acid was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 25 μm. From the measurement results of IR spectrum, it was confirmed that 1707 cm$^{-1}$ and 1773 cm$^{-1}$ had absorption peculiar to an imide group, and the optical film was made of polyimide.

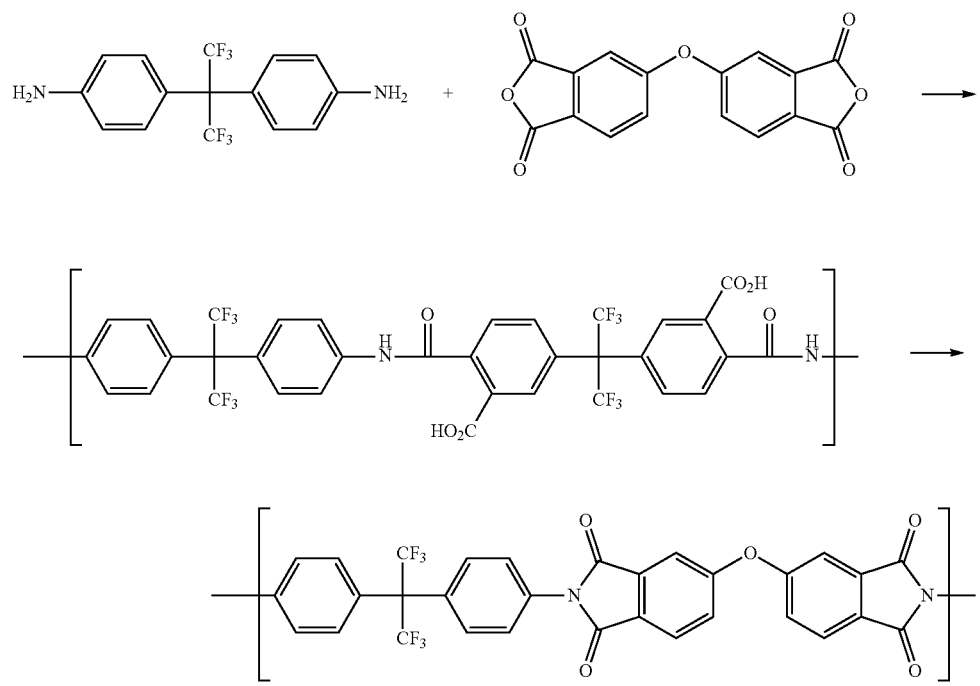

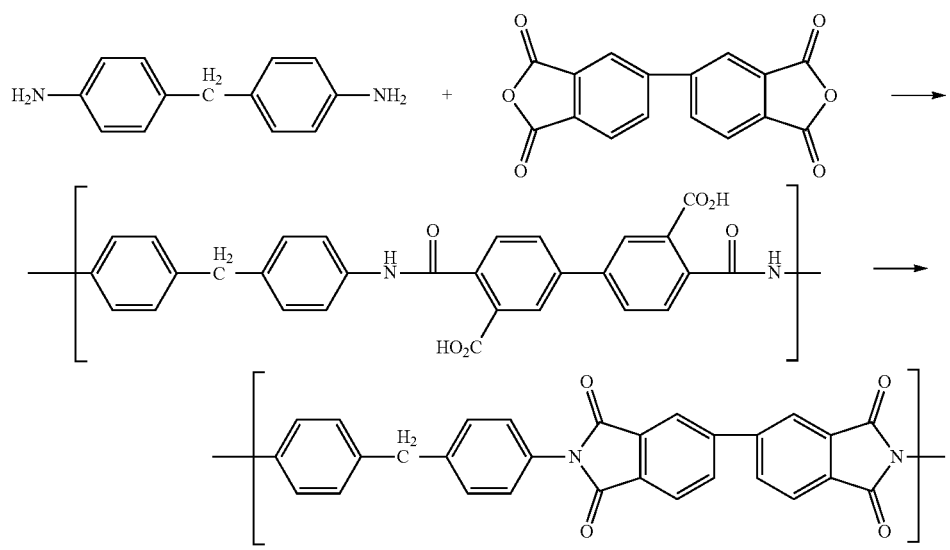

Comparative Example 9

15.8 g (70 mmol) of 2,2-bis(4-aminophenyl)propane (BIS-A-A) prepared in Synthesis Example 7 shown in the following formula and 20.6 g (70 mmol) of BPDA were added to a 500 mL three-necked flask equipped with a nitrogen inlet tube and a stirring blade, and 109 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. As a result of GPC measurement of the solution, Mw=119313 and Mw/Mn=6.0. The solution of polyamide acid was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 25 μm. From the measurement results of IR spectrum, it was confirmed that 1707 cm$^{-1}$ and 1773 cm$^{-1}$ had absorption peculiar to an imide group, and the optical film was made of polyimide.

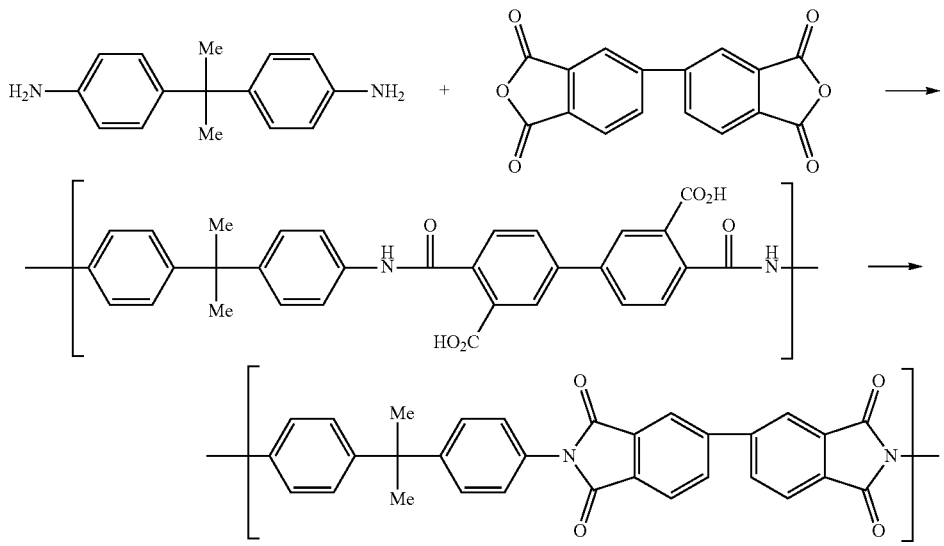

Comparative Example 101

12.5 g (37 mmol) of 2,2-bis(4-aminophenyl)hexafluoropropane (BIS-A-AF) and 11.0 g (37 mmol) of BPDA were added to a 500 mL three-necked flask equipped with a nitrogen inlet tube and a stirring blade, and 70.0 g of DMAc was further added as an organic solvent. This was followed by stirring at room temperature (20° C.) for 24 hours under a nitrogen atmosphere to obtain a reaction solution. This was followed by filtration under pressure to prepare a solution of polyamide acid. As a result of GPC measurement of the solution, Mw=92678 and Mw/Mn=5.3. The solution of polyamide acid was applied onto a glass substrate using a spin coater, followed by continuous heating at 130° C. for 30 minutes, 200° C. for 1 hour, and 300° C. for 1 hour while gradually raising the temperature to obtain a film on the glass substrate. The film thickness was 33 μm. From the measurement results of IR spectrum, it was confirmed that 1715 cm$^{-1}$ and 1778 cm$^{-1}$ had absorption peculiar to an imide group, and the film was made of polyimide.

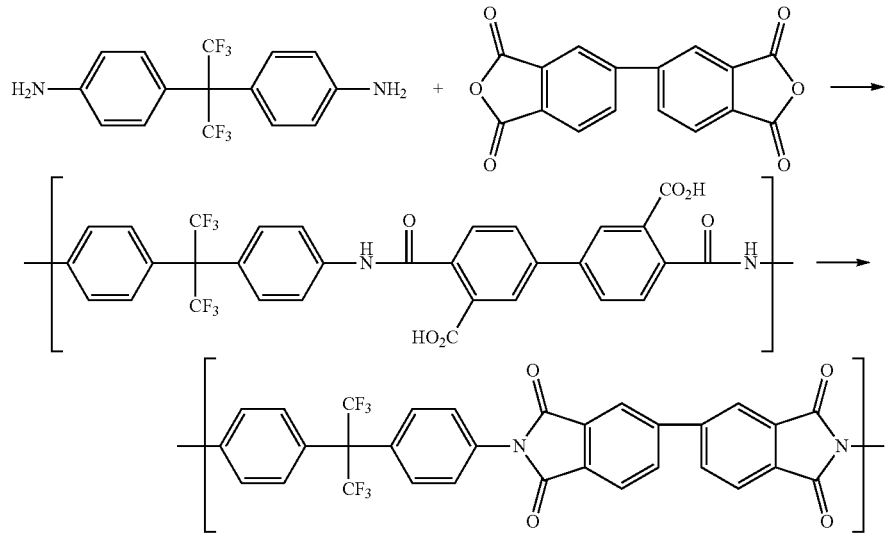

Comparative Example 11

11.9 g (60 mmol) of MDA and 17.7 g (60 mmol) of BPDA were added to a 500 mL three-necked flask equipped with a nitrogen inlet tube and a stirring blade, and 118 g of DMAc was further added as an organic solvent. This was followed by stirring at 50° C. for 30 minutes under a nitrogen atmosphere and further stirring at room temperature (20° C.) for 23 hours to obtain a solution of polyamide acid. 10.0 g (126 mmol) of pyridine and 12.9 g (126 mmol) of acetic anhydride were added in this order to the obtained reaction solution. This was followed by stirring at room temperature (20° C.) for 3 hours under a nitrogen atmosphere, but the imidized reaction solution gelled and therefore a solution of polyimide could not be obtained.

Comparative Example 12

15.8 g (70 mmol) of 2,2-bis(4-aminophenyl)propane (BIS-A-A) prepared in Synthesis Example 7 and 20.6 g (70 mmol) of BPDA were added to a 500 mL three-necked flask equipped with a nitrogen inlet tube and a stirring blade, and 109 g of DMAc was further added as an organic solvent. This was followed by stirring at room temperature (20° C.) for 23 hours under a nitrogen atmosphere to prepare a solution of polyamide acid. 11.7 g (147 mmol) of pyridine and 15.0 g (147 mmol) of acetic anhydride were added in this order to the obtained reaction solution. This was followed by stirring at room temperature (20° C.) for 3 hours under a nitrogen atmosphere, but the imidized reaction solution gelled and therefore a solution of polyimide could not be obtained.

Comparative Example 13

12.5 g (37 mmol) of 2,2-bis(4-aminophenyl)hexafluoro-propane (BIS-A-AF) and 11.0 g (37 mmol) of BPDA were added to a 500 mL three-necked flask equipped with a nitrogen inlet tube and a stirring blade, and 70.0 g of DMAc was further added as an organic solvent. This was followed by stirring at room temperature (20° C.) for 23 hours under a nitrogen atmosphere to prepare a solution of polyamide acid. 6.2 g (78 mmol) of pyridine and 8.0 g (78 mmol) of acetic anhydride were added in this order to the obtained reaction solution. This was followed by stirring at room temperature (20° C.) for 3 hours under a nitrogen atmosphere, but the imidized reaction solution gelled and therefore a solution of polyimide could not be obtained.

Comparative Example 141

15 g (56 mmol) of 1,1,1-trifluoro-2,2-bis (4-aminophenyl) ethane (BIS-A-EF) shown in the following formula and 18.2 g (56 mmol) of BTDA were added to a 500 mL three-necked flask equipped with a nitrogen inlet tube and a stirring blade, and 133 g of DMAc was further added as an organic solvent. This was followed by stirring at room temperature (20° C.) for 24 hours under a nitrogen atmosphere to obtain a reaction solution. Thereafter, DMAc was added to dilute the reaction solution which was then filtered under pressure to prepare a solution of polyamide acid. 9.4 g (118 mmol) of pyridine and 12.1 g (118 mmol) of acetic anhydride were added in this order to the obtained reaction solution which was then stirred at room temperature (20° C.) for 3 hours under a nitrogen atmosphere to carry out imidization. Thereafter, DMAc was added to dilute the imidized reaction solution which was then filtered under pressure to prepare a solution of polyimide. As a result of GPC measurement of the solution, Mw=87,000 and Mw/Mn=2.6. The solution of polyimide was applied onto a glass substrate using a spin coater, followed by continuous heating at 130° C. for 30 minutes, 200° C. for 1 hour, and 300° C. for 1 hour while gradually raising the temperature to obtain an optical film on the glass substrate. The film thickness was 30 μm. From the measurement results of IR spectrum, it was confirmed that 1718 cm$^{-1}$ and 1780 cm$^{-1}$ had absorption peculiar to an imide group, and the optical film was made of polyimide.

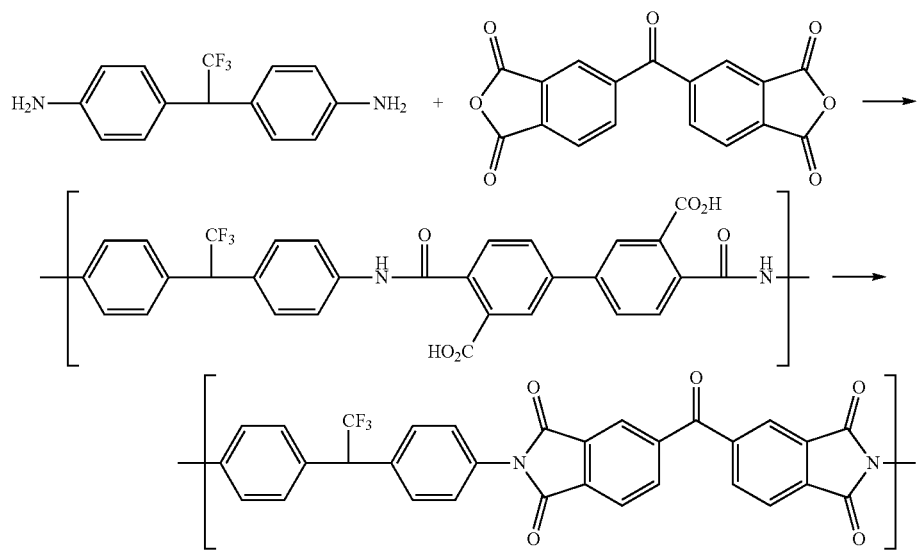

[Solvent Solubility and Processability]

The solvent solubility and processability of the polyimide obtained in each of Examples and Comparative Examples were measured.

The imidized reaction solution obtained in each of Examples and Comparative Examples was adjusted to a polymer solid content concentration of 2% by mass by adding each of solvents (DMAc, NMP, DMF), and was vibrated and stirred at 30° C. for 1 hour at a shaking speed of 100 rpm while keeping the temperature constant in a water bath using a constant temperature shaking water tank (Model: "UNI THERMO SHAKER NTS-1300", manufactured by Tokyo Rikakikai Co., Ltd.). Then, the presence of solids in the obtained polyimide solution was visually confirmed. The case where there were no solids was evaluated as having good solvent solubility (◯), and the case where there were solids was evaluated as having poor solvent solubility (x). Further, the obtained polyimide solution was applied to abase material to form a film, and it was visually confirmed whether or not a film having a uniform thickness could be obtained. The case where a film having a uniform thickness was obtained was evaluated as having good processability (◯), and the case where a film having a non-uniform thickness was obtained was evaluated as having poor processability (x). The results are shown in the table below.

In Examples 1 to 9, it was confirmed that all the obtained polyamide acids were soluble in organic solvents. From Examples 4, 5, 6, 8, 9, and 10, the polyimide consisting of a diamine having an asymmetric skeleton was obtained as a uniform high-viscosity liquid, had appropriate processability, and therefore could be formed into a film. In Comparative Examples 11 to 13, in a case where BPDA was used as the acid anhydride, the imidized reaction solution gelled and did not have appropriate processability, so that a film could not be obtained. Therefore, it was found that the polyamide acids and the polyimides of Examples had excellent solubility in an organic solvent, had appropriate processability, and therefore could be formed into a film.

TABLE 1

| Example No. | Diamine | Acid anhydride | Solvent solubility | Processability |
|---|---|---|---|---|
| Example 4 | BIS-3, 5-AX-EF | 6FDA | ◯ | ◯ |
| Example 5 | BIS-2, 5-AX-EF | 6FDA | ◯ | ◯ |
| Example 6 | BIS-2, 3-AX-EF | 6FDA | ◯ | ◯ |
| Example 8 | BIS-3, 5-AX-EF | ODPA | ◯ | ◯ |
| Example 9 | BIS-3-AT-EF | BPDA | ◯ | ◯ |
| Example 10 | BIS-3, 5-AX-EF | BPDA | ◯ | ◯ |
| Comparative Example 11 | MDA | BPDA | X (gelled) | X |
| Comparative Example 12 | BIS-A-A | BPDA | X (gelled) | X |
| Comparative Example 13 | BIS-A-AF | BPDA | X (gelled) | X |

[Transparency and Heat Resistance]

The transparency of the film consisting of the polyimide obtained in each of Examples 1 to 6 and Comparative Examples 1 to 4 was evaluated by measuring the light transmittance (T400) at a wavelength of 400 nm. The heat resistance of the film was evaluated by measuring the glass transition temperature and the 5% weight loss temperature ($Td_5$). The results are shown in Table 2.

TABLE 2

| | Diamine | Acid anhydride | T400 [%] | Tg [° C.] | Td5 [° C.] |
|---|---|---|---|---|---|
| Example 1 | BIS-A-AF | 6FDA | 64.5 | 316 | 507 |
| Example 2 | BIS-3-AT-EF | 6FDA | 81.6 | 312 | 493 |
| Example 3 | BIS-2-AT-EF | 6FDA | 58.0 | 309 | 479 |
| Example 4 | BIS-3, 5-AX-EF | 6FDA | 88.3 | 325 | 482 |
| Example 5 | BIS-2, 5-AX-EF | 6FDA | 73.0 | 333 | 480 |
| Example 6 | BIS-2, 3-AX-EF | 6FDA | 85.1 | 351 | 443 |
| Comparative Example 1 | MDA | 6FDA | 37.7 | 299 | 518 |
| Comparative Example 2 | BIS-A-A | 6FDA | 33.3 | 309 | 513 |
| Comparative Example 3 | BIS-A-AF | 6FDA | 77.3 | 295 | 519 |
| Comparative Example 4 | TFMB | 6FDA | 81.5 | 332 | 530 |

Examples 1 to 6 had higher transmittance and Tg values as compared with Comparative Examples 1 and 2.

Examples 2, 4, and 6 had a higher transmittance value as compared with Comparative Example 3. In addition, Examples 1 to 6 had a higher Tg value as compared with Comparative Example 3.

Examples 2, 4, and 6 had a higher transmittance value as compared with Comparative Example 4. In addition, Examples 5 and 6 had a higher Tg value as compared with Comparative Example 4.

As described above, it was shown that the polyimide of the present embodiment has excellent transparency and heat resistance.

Further, Examples 2, 4, and 6 in which a diamine having a methyl group in an aromatic in the polyimide of the present embodiment was used had a particularly high transmittance value.

Table 3 shows the evaluation results of the transparency and heat resistance of the optical film using ODPA as the acid anhydride.

TABLE 3

|  | Diamine | Acid anhydride | T400 [%] | Tg [° C.] | Td5 [° C.] |
|---|---|---|---|---|---|
| Example 7 | BIS-3-AT-EF | ODPA | 54.0 | 295 | 460 |
| Example 8 | BIS-3, 5-AX-EF | ODPA | 65.2 | 327 | 437 |
| Comparative Example 5 | MDA | ODPA | 26.7 | 270 | 523 |
| Comparative Example 6 | BIS-A-A | ODPA | 21.0 | 286 | 509 |
| Comparative Example 7 | BIS-A-AF | ODPA | 47.6 | 289 | 531 |

Similar to the case of using 6FDA as the acid anhydride, the films of Examples were shown to have excellent transparency and heat resistance. Therefore, it was found that the polyimide of the present embodiment has excellent transparency and heat resistance.

Table 4 shows the evaluation results of the transparency and heat resistance of the optical film using BPDA as the acid anhydride.

TABLE 4

|  | Diamine | Acid anhydride | T400 [%] | Tg [° C.] | Td5 [° C.] |
|---|---|---|---|---|---|
| Example 9 | BIS-3-AT-EF | BPDA | 55.1 | 340 | 477 |
| Example 10 | BIS-3, 5-AX-EF | BPDA | 58.8 | 373 | 457 |
| Comparative Example 8 | MDA | BPDA | 0.1 | 307 | 541 |
| Comparative Example 9 | BIS-A-A | BPDA | 0.3 | 344 | 521 |
| Comparative Example 10 | BIS-A-AF | BPDA | 20.0 | 334 | 534 |

Similar to the case of using 6FDA and ODPA as acid anhydrides, the films of Examples were shown to have excellent transparency and heat resistance.

Table 5 shows the evaluation results of the transparency of the optical film using BTDA as the acid anhydride.

TABLE 5

|  | Diamine | Acid anhydride | T400 [%] |
|---|---|---|---|
| Example 11 | BIS-3-AT-EF | BTDA | 55.0 |
| Example 12 | BIS-2, 5-AX-EF | BTDA | 25.0 |

TABLE 5-continued

|  | Diamine | Acid anhydride | T400 [%] |
|---|---|---|---|
| Comparative Example 14 | BIS-A-EF | BTDA | 3.7 |

It was found that the films of Examples had superior transparency as compared with the film of Comparative Example 14.

From the above results, it was shown that the optical film and the substrate for a display device, each containing the polyimide of the present embodiment, had excellent transparency and heat resistance.

This application claims priority based on Japanese Patent Application No. 2019-019823 filed on Feb. 6, 2019, the disclosure of which is herein incorporated by reference in its entirety.

The invention claimed is:

1. A polyimide having a repeating unit represented by General Formula [1], with the proviso that a polyimide having a repeating unit represented by General Formula [3] is excluded:

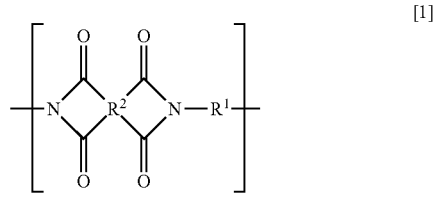

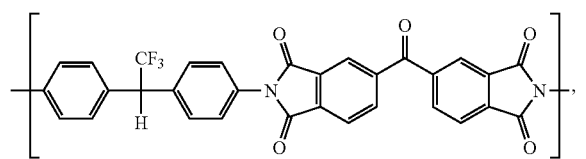

wherein, in General Formula [1], $R^1$ is a divalent organic group represented by General Formula [2], and $R^2$ is a tetravalent organic group, and

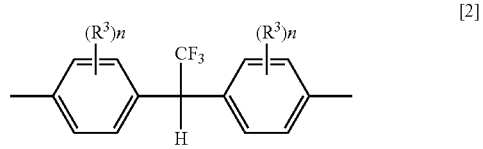

wherein, in General Formula [2], n is an integer of 1 to 4, and $R^3$ each independently represents an alkyl group.

2. The polyimide according to claim 1, wherein $R^1$ is at least one divalent organic group selected from the following:

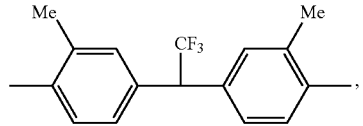

3. The polyimide according to claim 1, wherein $R^2$ is at least one tetravalent organic group selected from the following:

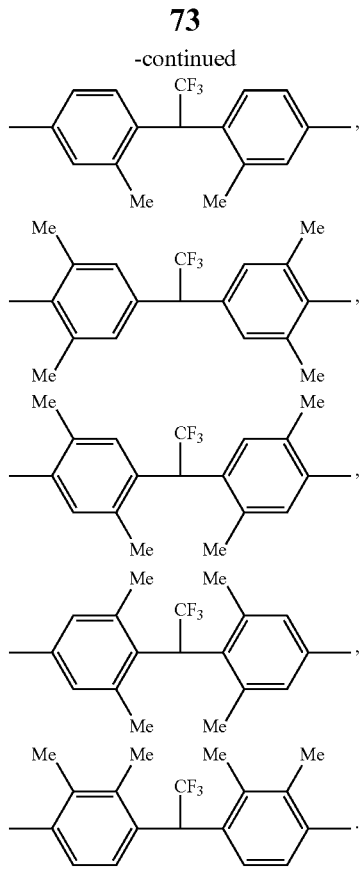
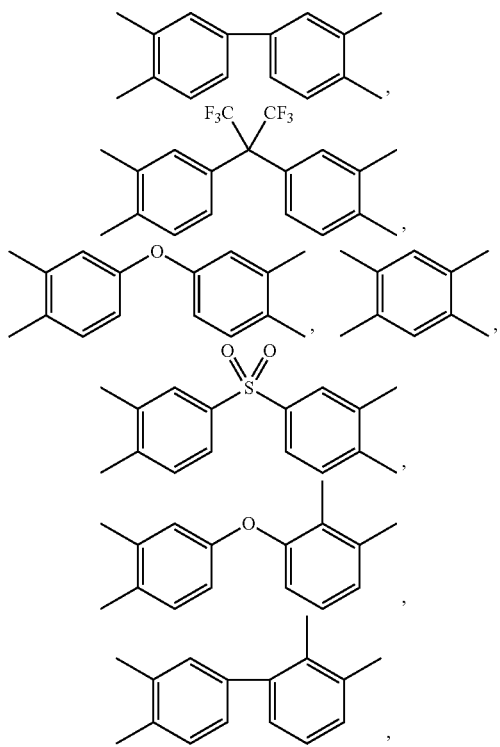
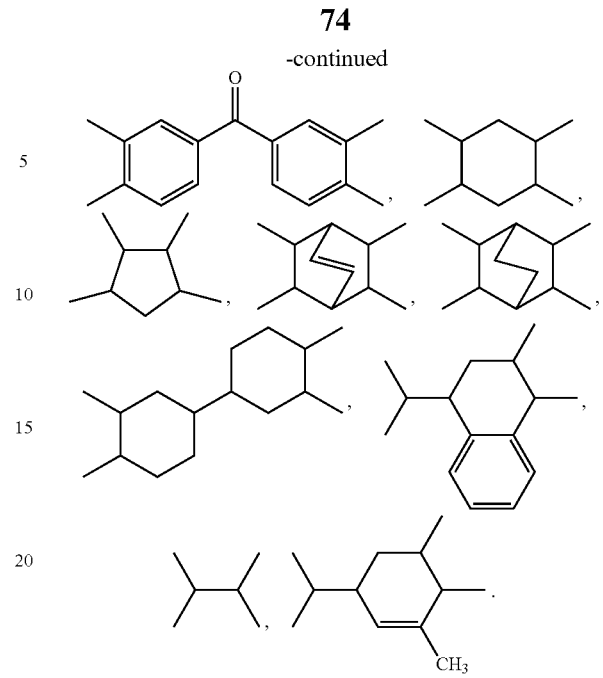

4. The polyimide according to claim 1, wherein a weight average molecular weight is equal to or more than 1,000 and equal to or less than 1,000,000.

5. A polyamide acid having a repeating unit represented by General Formula [1A], with the proviso that a polyamide acid having a repeating unit represented by General Formula [3A] is excluded:

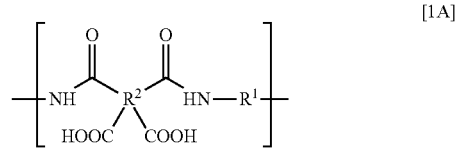

[1A]

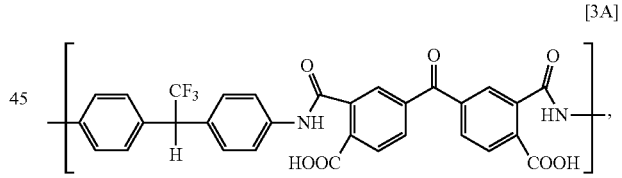

[3A]

wherein, in General Formula [1A], $R^1$ is a divalent organic group represented by General Formula [2], and $R^2$ is a tetravalent organic group, and

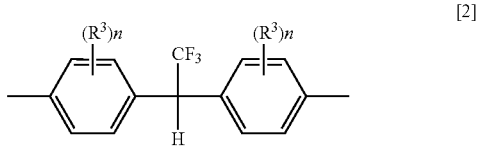

[2]

wherein, in General Formula [2], n is an integer of 1 to 4, and $R^3$ each independently represents an alkyl group.

6. The polyamide acid according to claim 5, wherein $R^1$ is at least one divalent organic group selected from the following:

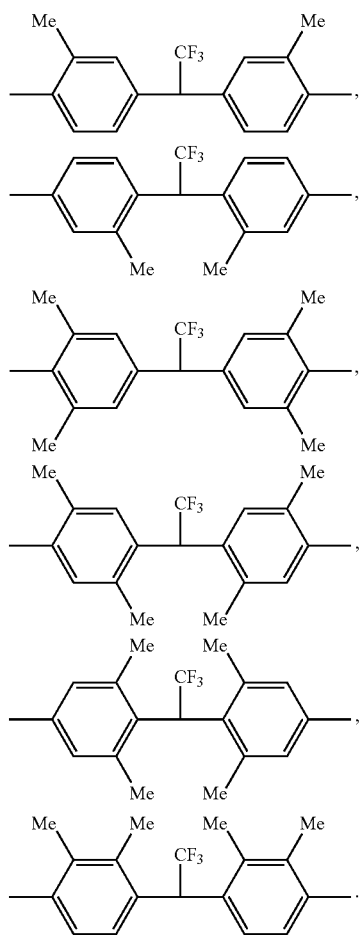

7. The polyamide acid according to claim 5, wherein R² is at least one tetravalent organic group selected from the following:

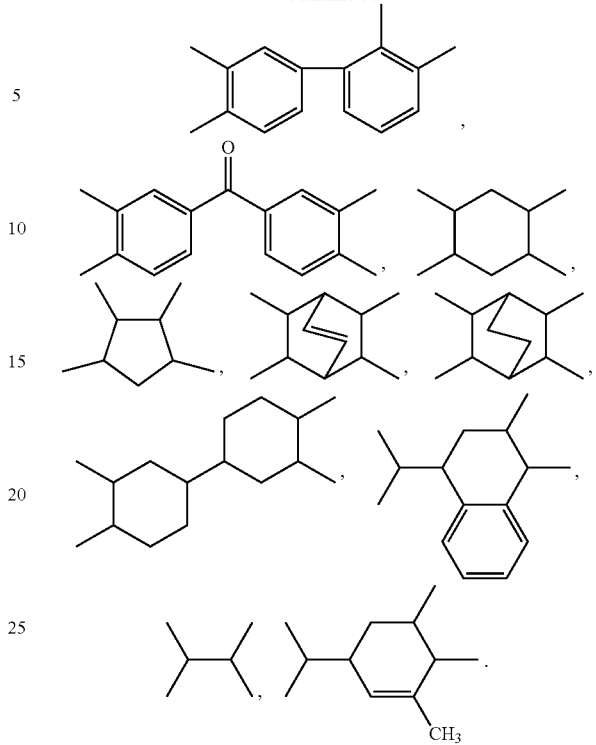

8. The polyamide acid according to claim 5, wherein a weight average molecular weight is equal to or more than 1,000 and equal to or less than 1,000,000.

9. A polyimide solution comprising:
   the polyimide according to claim 1; and
   an organic solvent.

10. The polyimide solution according to claim 9, wherein the organic solvent is at least one selected from the group consisting of an amide-based solvent, an ether-based solvent, an aromatic hydrocarbon-based solvent, a halogen-based solvent, and a lactone-based solvent.

11. The polyimide solution according to claim 9, wherein the polyimide is in an amount of equal to or more than 0.1% by mass and equal to or less than 50% by mass with respect to an entire polyimide solution.

12. A polyamide acid solution comprising:
    the polyamide acid according to claim 5; and
    an organic solvent.

13. The polyamide acid solution according to claim 12, wherein the organic solvent is at least one selected from the group consisting of an amide-based solvent, an ether-based solvent, an aromatic hydrocarbon-based solvent, a halogen-based solvent, and a lactone-based solvent.

14. The polyamide acid solution according to claim 12, wherein the polyamide acid is in an amount of equal to or more than 0.1% by mass and equal to or less than 50% by mass with respect to an entire polyamide acid solution.

15. An optical film comprising:
    the polyimide according to claim 1.

16. An optical film comprising:
    the polyamide acid according to claim 5.

17. An optical film comprising:
    the polyimide according to claim 1; and
    the polyamide acid according to claim 5.

18. A display device comprising:
    the optical film according to claim 15.

19. A method for producing a polyimide according to claim 1, the method comprising:
   a step of polycondensing a diamine represented by General Formula [2A]:

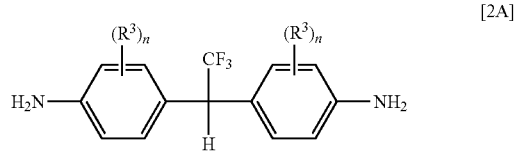

[2A]

wherein, in General Formula [2A], R³ each independently represents an alkyl group, and n is an integer of 1 to 4, with a tetracarboxylic dianhydride represented by General Formula [4]:

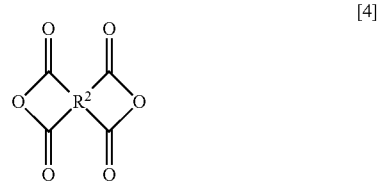

[4]

wherein, in General Formula [4], R² is a tetravalent organic group to obtain the polyimide having a repeating unit represented by General Formula [1].

20. The method for producing a polyimide according to claim 19, wherein the step of polycondensing the diamine represented by General Formula [2A] with the tetracarboxylic dianhydride represented by General Formula [4] to obtain the polyimide having a repeating unit represented by General Formula [1] includes:
   a step of reacting the diamine represented by General Formula [2A] with the tetracarboxylic dianhydride represented by General Formula [4] to obtain a polyamide acid having a repeating unit represented by General Formula [1A], with the proviso that a polyamide acid having a repeating unit represented by General Formula [3A] is excluded:

[1A]

[3A]

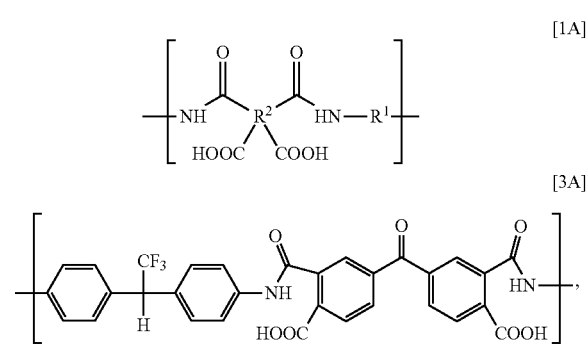

wherein, in General Formula [1A], R¹ has the same definition as R¹ in General Formula [1], and R² has the same definition as R² in General Formula [1]; and
   a step of dehydrating and ring-closing the polyamide acid represented by General Formula [1A] to be converted into the polyimide represented by General Formula [1].

21. A method for producing an optical film or a display device, comprising:
   a step of applying the polyimide solution according to claim 9 or the polyamide acid solution according to claim 12 to a supporting base material;
   a step of removing a solvent contained in the polyimide solution or the polyamide acid solution, followed by drying to produce a resin film containing polyimide or polyamide acid; and
   a step of heat-treating and curing the resin film.

22. The method for producing an optical film or a display device according to claim 21, wherein the supporting base material is at least one selected from the group consisting of glass, silicon wafer, stainless steel, alumina, copper, nickel, polyethylene terephthalate, polyethylene glycol terephthalate, polyethylene glycol naphthalate, polycarbonate, polyimide, polyamide imide, polyether imide, polyether ether ketone, polypropylene, polyether sulfone, polyphenylene sulfone, and polyphenylene sulfide.

23. The method for producing an optical film or a display device according to claim 21, wherein the step of applying the polyimide solution or the polyamide acid solution to the supporting base material includes a step of applying the solution such that a film thickness is equal to or more than 1 μm and equal to or less than 1,000 μm.

24. The method for producing an optical film or a display device according to claim 21, wherein the step of drying is carried out at a temperature of equal to or higher than 50° C. and equal to or lower than 250° C.

25. The method for producing an optical film or a display device according to claim 21, wherein the step of heat-treating the resin film is carried out at a temperature of equal to or higher than 150° C. and equal to or lower than 400° C.

26. A polyimide having a repeating unit represented by General Formula [1], with the proviso that a polyimide having a repeating unit represented by General Formula [3] is excluded:

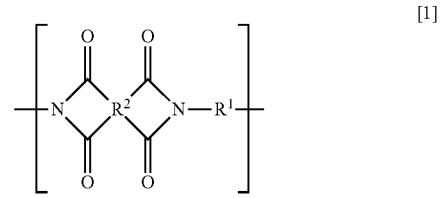

[1]

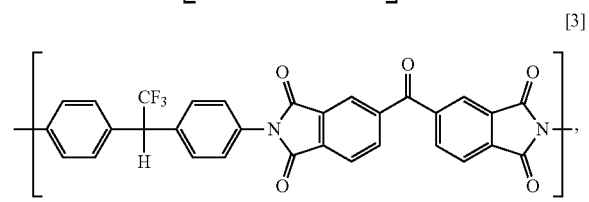

[3]

wherein, in General Formula [1], R¹ is a divalent organic group represented by General Formula [2],

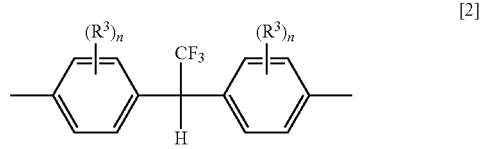

[2]

and $R^2$ is a tetravalent organic group selected from the following,
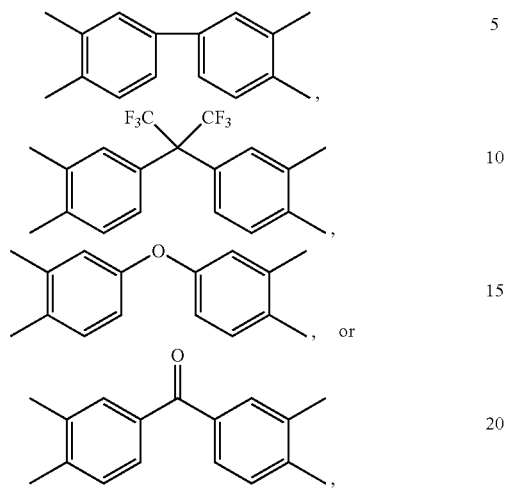
wherein, in General Formula [2], n is an integer of 1 to 4, and $R^3$ each independently represents an alkyl group.
* * * * *